US006093410A

United States Patent [19]
Peffly et al.

[11] Patent Number: 6,093,410
[45] Date of Patent: *Jul. 25, 2000

[54] PERSONAL CARE COMPOSITIONS

[75] Inventors: Marjorie Mossman Peffly, Cincinnati; Raymond Edward Bolich, Jr., Maineville; Peter Marte Torgerson, Washington Court House; Sanjeev Midha, Blue Ash, all of Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/964,325

[22] Filed: Nov. 5, 1997

[51] Int. Cl.$^7$ .................. A61K 7/00; A61K 7/06
[52] U.S. Cl. .................. 424/401; 424/70.1
[58] Field of Search .................. 424/401, 70.1, 424/78.03, 61; 514/63, 937

[56] References Cited

U.S. PATENT DOCUMENTS

| | | | |
|---|---|---|---|
| 4,584,356 | 4/1986 | Crivello | 525/479 |
| 4,659,777 | 4/1987 | Riffle et al. | 525/100 |
| 4,689,289 | 8/1987 | Crivello | 430/270 |
| 4,693,935 | 9/1987 | Mazurek | 428/352 |
| 4,728,571 | 3/1988 | Clemens et al. | 428/352 |
| 4,733,677 | 3/1988 | Gee et al. | 132/7 |
| 4,871,529 | 10/1989 | Sramek | 424/47 |
| 5,017,221 | 5/1991 | Legrow et al. | 106/2 |
| 5,032,460 | 7/1991 | Kantner et al. | 428/449 |
| 5,244,598 | 9/1993 | Merrifield et al. | 252/314 |
| 5,302,657 | 4/1994 | Huhn et al. | 524/588 |
| 5,362,485 | 11/1994 | Hayama et al. | 424/70 |
| 5,468,477 | 11/1995 | Kumar et al. | 424/78.17 |
| 5,523,365 | 6/1996 | Geck et al. | 526/194 |
| 5,578,298 | 11/1996 | Berthiaume et al. | 424/70.122 |
| 5,618,524 | 4/1997 | Bolich, Jr. et al. | 424/70.12 |
| 5,658,557 | 8/1997 | Bolich, Jr. et al. | 424/70.12 |
| 5,658,577 | 8/1997 | Fowler et al. | 424/401 |

FOREIGN PATENT DOCUMENTS

| | | | |
|---|---|---|---|
| 0268982 A2 | 6/1988 | European Pat. Off. | A61K 7/06 |
| 0459500 B1 | 12/1991 | European Pat. Off. | C08G 77/10 |
| 0463431 A2 | 1/1992 | European Pat. Off. | C08J 3/03 |
| 0560516 A1 | 9/1993 | European Pat. Off. | A61K 7/06 |
| WO 9714395 A1 | 4/1997 | WIPO | A61K 7/06 |

*Primary Examiner*—Thurman K. Page
*Assistant Examiner*—S. Howard
*Attorney, Agent, or Firm*—Lucy Elandjian; Joan B. Tucker

[57] ABSTRACT

Emulsion compositions, suitable for personal care applications such as hair styling, and other applications, are disclosed. The compositions comprise:

a) a silicone functional polymer having the formula selected from the group consisting of:

$(AB)_n$; ABA; BAB;

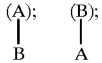

and mixtures thereof;

wherein B is a silicone moiety comprising repeating units of:

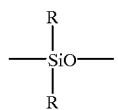

R is independently, C1–C30 alkyl, aryl, alkylaryl, haloalkyl, H, or C1–C6 alkoxy, wherein the weight average molecular weight of each silicone moiety B is independently from about 1500 to about 50,000;

A is a polar polymeric moiety which is soluble or dispersible in mixtures of ethanol and water containing less than 60% ethanol by weight; and n is an integer of 1 or greater;

wherein the molecular weight of the silicone functional polymer is at least about 2,000.

b) an organopolysiloxane emulsion comprising:

(i) a polyorganosiloxane dispersed as particles in the emulsion, the polyorganosiloxane having an average particle size of less than about 150 nanometers, and (ii) a surfactant system for dispersing the organopolysiloxane in the emulsion;

c) a carrier comprising at least about 0.5%, by weight of the composition, of a first solvent selected from the group consisting of water; water soluble organic solvents; organic solvents which are strongly to moderately strong in hydrogen-bonding parameter; and mixtures thereof; wherein the first solvent is other than $C_1$–$C_3$ monohydric alcohol, $C_1$–$C_3$ ketone and $C_1$–$C_3$ ether;

wherein the silicone functional polymer is present in an amount effective to stabilize the emulsion in the personal care composition.

25 Claims, No Drawings

PERSONAL CARE COMPOSITIONS

TECHNICAL FIELD

The present invention relates to compositions including silicone emulsions, especially microemulsions, and corresponding applications of the compositions, e.g., in personal care areas such as hair care, skin care, and nail care. The compositions are especially useful, e.g., in hair styling applications. The invention further relates to stable compositions containing a silicone emulsion, especially microemulsions, and lower monohydric alcohol, and corresponding applications of the compositions.

BACKGROUND OF THE INVENTION

Silicone emulsions have been used in a variety of applications in the areas of personal care (e.g., hair, skin or nail care), household care, automotive care, and coatings. When used, the stability of the emulsion is generally important in order to provide a highly functional and esthetically pleasing product. However, formulations in these areas tends to be complex, requiring a number of ingredients for different purposes, with potential for incompatibilities. For example, silicone emulsions tend to be unstable in compositions containing lower alcohols, resulting in phase separation of the composition. Other incompatibilities in the system, e.g., polymer—polymer or polymer-surfactant interactions, can also result in phase separation.

For example, silicone emulsions have been used in hair styling compositions, e.g., hairsprays, mousses, gels, lotions and the like. Such compositions provide temporary setting benefits and can usually be removed by water or by shampooing. The materials used in these types of hair styling compositions are generally resins, gums, and adhesive polymers which are capable of imparting style or shape to the hair.

Many of these products also contain lower alcohols in order to obtain good films of the polymer in a short period of time.

Many people desire a high level of style retention, or hold, from a styling product. Unfortunately, most current hair styling products having good hold characteristics suffer from the disadvantages of being either too stiff, not smooth or too sticky upon drying. Stiff compositions tend to be brittle and break down under common stresses such as wind, brushing, combing. Stiff compositions also tend to feel and look unnatural. Sticky compositions overcome many of the foregoing disadvantages of stiff compositions, because sticky compositions tend to be more forgiving, i.e., flexible, under stress and allow for restyling of the hair. However, sticky compositions have the disadvantage of leaving the hair with a heavy, coated feel and with a limp and unattractive appearance. Also, sticky compositions cause the hair to quickly become soiled from common contaminant sources such as dust, dirt, lint, sebum, etc.

When incorporated into a hair styling composition, silicones tend to provide a desirably smooth or soft hair feel. Unfortunately, silicone emulsions tend to be difficult to formulate in hair styling compositions, which typically contain lower alcohols. As discussed above, such compositions tend to phase separate. This phase separation is not only undesirable for visual esthetic reasons, but for performance reasons as well. When the product phase separates, hold and/or hair feel properties of the product tend to be negatively impacted.

Therefore, a need exists for hair styling compositions providing good style retention without the disadvantages of stiff or sticky compositions. There is a particular need for hair styling compositions containing lower alcohols providing good style retention without the disadvantages of stiff or sticky compositions.

A variety of personal care products for treatment of skin and nails are also known. Many of these products contain alcohols, generally to provide a volatility to the product for a desired astringency, application or other reason. These products may also contain a silicone for imparting a desirable skin feel. Examples of such products include deodorants, antiperspirants, after-shave lotions, nail polish, nail polish remover, wet wipes, leather conditioners, and spray lubricants. Such products containing lower alcohols and silicone emulsions also tend to suffer from phase separation, which negatively impacts visual esthetics and/or performance of the product. Therefore, a need exists for topical compositions for treating the skin or nails, containing lower alcohols and silicone emulsions, which are also stable.

It has been discovered that certain silicone functional polymers can be used to stabilize silicone emulsions, silicone microemulsions or a composition containing such emulsions in the presence of lower alcohols, e.g., $C_1$–$C_3$ monohydric alcohols, which may be included in the composition. Stability is provided even where the composition contains relatively high levels of lower alcohol. While stability with respect to $C_1$–$C_3$ monohydric alcohols, and especially ethanol, propanol and isopropanol, is of greatest interest because of their widespread use in commercial applications, superior stability is also provided to compositions containing $C_1$–$C_3$ ketones and ethers. Such stability is useful in a variety of applications, including applications in the areas of personal care, household care, automotive care and coatings.

It is an object of the invention to provide novel silicone functional polymers which are useful for stabilizing silicone emulsions in the presence of an alcohol.

Another object of the invention is to provide stable compositions containing certain silicone functional polymers and a suitable carrier, especially carriers containing lower alcohols. It is yet another object of the invention to provide such compositions which also contain a silicone emulsion.

It is another object of the invention to provide such polymers and compositions which are suitable for applications in the personal care area, including hair care, skin care and nail care applications.

It is another object of the invention to provide such polymers and compositions which are suitable for hair styling, e.g., hair sprays, mousses, gels, lotions and the like.

It is another object of this invention to provide hair styling compositions that provide good style retention without unacceptable stiffness or stickiness. Another object of this invention is to provide hair styling compositions that both look and feel natural.

It is another object of this invention to provide methods for styling and holding hair.

These and other objects will become readily apparent from the detailed description which follows.

SUMMARY OF THE INVENTION

The present invention relates to personal care compositions, e.g., compositions which are suitable for application to the skin, hair or nails. The compositions comprise:

a) a silicone functional polymer having the formula selected from the group consisting of:

$(AB)_n$; ABA; BAB;

and mixtures thereof;
wherein B is a silicone moiety comprising repeating units of:

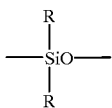

R is independently, C1–C30 alkyl, aryl, alkylaryl, haloalkyl, H or C1–C6 alkoxy, wherein the weight average molecular weight of each silicone moiety B is independently from about 1500 to about 50,000; and A is a polar polymeric moiety which is soluble or dispersible, preferably soluble or microdispersible, in mixtures of ethanol and water containing less than 60% ethanol by weight;

n is an integer of 1 or greater;

wherein the molecular weight of the silicone functional polymer is at least about 2000, preferably from about 2,000 to about 1,000,000;

b) an organopolysiloxane emulsion comprising:

(i) a polyorganosiloxane dispersed as particles in the emulsion, the polyorganosiloxane having an average particle size of less than about 150 nanometers, and (ii) a surfactant system for dispersing the organopolysiloxane in the emulsion;

c) a carrier comprising at least about 0.5%, by weight of the composition, of a first solvent selected from the group consisting of water; water soluble organic solvents; organic solvents which are strongly to moderately strong in hydrogen-bonding parameter; and mixtures thereof; wherein the first solvent is other than $C_1$–$C_3$ monohydric alcohol, $C_1$–$C_3$ ketone and $C_1$–$C_3$ ether, wherein the silicone functional polymer is present in an amount effective to stabilize the emulsion in the personal care composition.

In a preferred embodiment, the composition further comprises a second solvent selected from $C_1$–$C_3$ monohydric alcohols, $C_1$–$C_3$ ketones, $C_1$–$C_3$ ethers, and mixtures thereof preferably a $C_1$–$C_3$ monohydric alcohol. Compositions of this type preferably comprise water as the first solvent. The composition may comprise a hair styling polymer.

DETAILED DESCRIPTION OF THE INVENTION

The essential components of the present invention are described below. Also included is a nonexclusive description of various optional and preferred components useful in embodiments of the present invention.

The present invention can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All molecular weights are weight average molecular weights and are given in units of grams per mole.

All ingredient levels are in reference to the active level of that ingredient, and are exclusive of solvents, by-products, or other impurities that may be present in commercially available sources, unless otherwise indicated.

All measurements made are at ambient room temperature, which is approximately 73° F., unless otherwise designated.

All documents referred to herein, including all patents, patent applications, and printed publications, are hereby incorporated by reference in their entirety in this disclosure.

Preferred components and compositions herein are those suitable for application to human hair, skin, or nails. The term "suitable for application to human hair, skin or nails" or the like, as used herein, means that the compositions or components thereof so described are suitable for use in contact with human hair, skin (including the scalp) or nails, respectively, without undue toxicity, incompatibility, instability, allergic response, and the like.

The components of the compositions hereof are selected such that the total composition will be compatible. As used herein, compatible means there is no marked phase separation, e.g., excessive cloudiness, layering or precipitation of the composition which negatively impacts the esthetic or functional properties of the composition in a significant manner.

Preferred compositions are those wherein the mixture of essential components, namely the silicone functional polymer, silicone emulsion, and carrier is a substantially homogeneous solution or dispersion (preferably a microdispersion), more preferably substantially clear to translucent in appearance. Preferred final personal care compositions are those also characterized by these properties.

Preferred compositions are those wherein the mixture of essential components provides a % transmittance of at least about 50% at a wavelength of 460 nm as determined by standard spectroscopy methods. Preferred final personal care compositions are those also characterized by these properties.

Silicone Functional Polymers

The compositions of the present invention comprise a silicone functional polymer for providing stability to the silicone microemulsion in the composition. One or more silicone functional polymers may be used. The silicone functional polymer is used in an amount effective to stabilize the silicone microemulsion in the personal care composition (such that the composition will be compatible). The silicone functional polymer assists to prevent or minimize coagulation, agglomeration or coalescence of teh emulsion particles and their subsequent settling or rising to the surface. Some settling or rising is acceptable, although not preferred, provided that the particles are readily redispersed by light agitation such as shaking. Generally from about 0.01% to about 20%, preferably from about 0.1% to about 15%, more preferably from about 0.5% to about 10% of the silicone functional polymer is used.

A variety of silicone functional polymers are suitable in the present invention. Particular polymers will be selected by the skilled artisan considering the solubility of the polymer in the composition and the ionicity of the composition.

Suitable silicone functional polymers are those which are soluble or dispersible (preferably microdispersible) in the carrier described herein in the weight ratios employed in the composition. Solubility or dispersibilty is determined at ambient conditions of temperature and pressure (25° C., 101.3 kPa (1 Atm)), and after neutralization of the polymer, if any.

Exemplary silicone functional polymers include the following:

(AB)$_n$, ABA, BAB,

Wherein B is a silicone moiety comprising repeating units of:

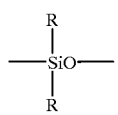

R can be independently, C1–C30 alkyl, aryl (e.g., phenyl), alkylaryl (e.g., styryl), haloalkyl, H, and C1–C6 alkoxy, wherein the molecular weight of the silicone moiety is about 1500 to about 50,000, more preferably about 2,000 to about 40,000, and most preferably about 2,000 to about 30,000;

A is a polar polymeric moiety of any monomer composition provided that the silicone functional polymer is soluble or dispersible (preferably micro-dispersible) at 25° C., 101.3 kPa (1 Atm) in mixtures of ethanol and water where the ethanol content is less than 60% by weight. Solubility/dispersibility in such mixtures is present where the resulting mixture is substantially clear to translucent in appearance and the mixture is compatible. Suitable A moieties include acrylic and vinyl polymers, polyalkyloxazolines, proteins, sugars and polysaccharides. Exemplary acrylics and vinyls are as described below in reference to silicone graft polymers; and n is an integer of 1 or more, preferably 1.

The molecular weight of the silicone functional polymer is at least about 2000, preferably from about 2,000 to about 1,000,000, more preferably from about 2,000 to about 150,000, still more preferably from about 3,000 to about 50,000, and most preferably from about 3,000 to about 20,000.

Suitable silicone functional polymers include graft and block copolymers comprising silicone with a nonsilicone, polar polymer. Whether graft or block, these copolymers should satisfy the following four criteria:

(1) the silicone portion is covalently attached to the non-silicone portion;

(2) the molecular weight of the silicone portion is greater than 1500, preferably at least about 2,000, and up to about 50,000; and (3) the non-silicone portion must render the entire copolymer soluble or dispersible in the personal care composition vehicle.

Suitable silicone functional copolymers include the following:

(i) Silicone Graft Copolymers

Silicone graft copolymers suitable for the present invention are exemplified by the formulas

where the first structure has the silicone grafted to the non-silicone backbone, and the second has the non-silicone portion grafted to the silicone backbone, and x, y, p and s are as defined above.

Such graft copolymers can be prepared by a number of methods known to those skilled in the art, including:

1. Incorporation of silicone macromonomers in free radical polymerization. Such silicone functional polymers include the silicone graft copolymers described, along with methods of making them, in U.S. Pat. No. 5,658,557, Bolich et al., issued Aug. 19, 1997, U.S. Pat. No. 4,693,935, Mazurek, issued Sep. 15, 1987, and U.S. Pat. No. 4,728,571, Clemens et al., issued Mar. 1, 1988, each incorporated herein by reference.

2. Incorporation of silicone macromonomer in atom transfer radical polymerization. A method of making these types of polymers is generally described in Beers et al, "The Use of 'Living' Radical Polymerization to Synthesize Graft Copolymers," *Polymer Preprints*, pp 571–572, March, 1996, incorporated herein by reference.

3. Incorporation of vinyl polymeric grafts onto a silicone backbone by chain transfer to a pendant sulfhydryl group. Such sulfur linked silicone copolymers are described in detail in U.S. Pat. No. 5,468,477, to Kumar et al., issued Nov. 21, 1995, and PCT Application No. WO 95/03776, assigned to 3M, published Feb. 9, 1995, which are incorporated by reference herein in their entirety. Additional patents with sulfur linked structures include U.S. Pat. No. 5,032,460, to Kanter et al, issued Jul. 16, 1991, assigned to 3M and U.S. Pat. No. 5,362,485, to Hayama et al, issued Nov. 8, 1994, assigned to Mitsubishi Chem. Co.

Preferred silicone functional polymers are the silicone graft copolymers described, along with methods of making them, in the above referenced and incorporated U.S. Pat. No. 5,658,557, Bolich et al., issued Aug. 19, 1997, U.S. Pat. No. 4,693,935, Mazurek, issued Sep. 15, 1987, and U.S. Pat. No. 4,728,571, Clemens et al., issued Mar. 1, 1988. In addition to stabilizing the silicone microemulsion, these silicone-containing copolymers provide hair conditioning and/or hair setting characteristics to the composition.

These polymers include copolymers having a molecular weight of from about 2,000 to about 1,000,000, which have a vinyl polymeric backbone comprising acrylate groups and having grafted to it monovalent siloxane polymeric moieties, the copolymer comprising C monomers and components selected from the group consisting of A monomers, B monomers, and mixtures thereof. A is at least one free radically polymerizable vinyl monomer, and the amount by weight of A monomer, when used, is up to about 90% of the total weight of all monomers in the copolymer. B is at least one reinforcing monomer copolymerizable with A, and the amount by weight of B monomer, when used, is up to about 98% of the total weight of all monomers in the copolymer. The B monomer is selected from the group consisting of polar monomers and macromers. At least one of the A or B monomers comprise an acrylate monomer. C comprises from about 0.01% to about 80% of the copolymer and is a polymeric monomer having a molecular weight of at least 1,500, preferably at least about 2,000, up to about 50,000 and the general formula

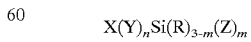

wherein

X is a vinyl group copolymerizable with the A and B monomers

Y is a divalent linking group

R is a hydrogen, lower alkyl (preferably $C_1$–$C_5$, more preferably $C_1$–$C_3$), aryl or alkoxy Z is a monovalent siloxane polymeric moiety having a number average molecular weight of at least about 1500, is essentially unreactive under copolymerization conditions, and is pendant from the vinyl polymeric backbone after copolymerization n is 0 or 1, and m is an integer from 1 to 3.

In another embodiment, the silicone-acrylate copolymer has a vinyl polymeric backbone comprising acrylate groups and grafted to the backbone a polydimethylsiloxane macromer having a weight average molecular weight of at least 1,500, preferably at least about 2,000, and up to about 50,000, preferably from about 2,000 to about 40,000, most preferably about 3000 to about 30,000.

The polymers should have a weight average molecular weight of from about 2,000 to about 1,000,000 (preferably from about 2,000 to about 150,000).

As used herein, "acrylate monomer" means acrylic acid and derivatives thereof e.g., esters of acrylic acid. The acid of derivatives may be substituted, e.g., with alkyl groups.

Representative examples of A (hydrophobic) monomers are acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol (2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred A monomers are the acrylic or methacrylic acid esters of $C_1$–$C_{18}$ alcohols, more preferably n-butyl methacrylate, isobutyl methacrylate, t-butyl acrylate, t-butyl methacrylate, 2-ethylhexyl methacrylate, methyl methacrylate, and mixtures thereof.

Representative examples of B monomers (hydrophilic) include acrylic acid, methacrylic acid, N,N-dimethylacrylamide, dimethylaminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (produced by the hydrolysis of vinyl acetate after polymerization) vinyl caprolactam, and mixtures thereof. Preferred B monomers include acrylic acid and derivatives thereof, vinyl pyrrolidone, and mixtures thereof. More preferred B monomers are N,N-dimethylacrylamide, dinethylaminoethyl methacrylate, quaternized dimethylaminoethyl methacrylate, vinyl pyrrolidone, and mixtures thereof.

Preferably, the C monomer has a formula selected from the following group:

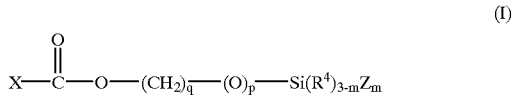

(I)

(II)

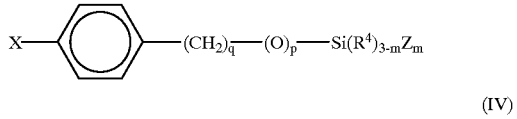

(III)

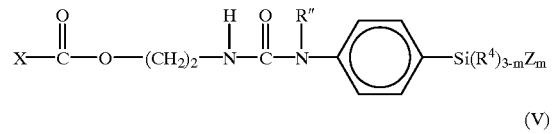

(IV)

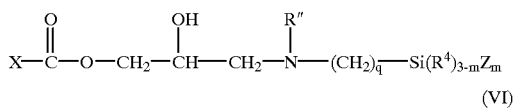

(V)

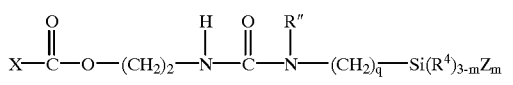

(VI)

In those structures, m is 1, 2 or 3 (preferably m=1); p is 0 or 1, preferably 0; R'' is alkyl or hydrogen; q (in all but (III) is an integer from 2 to 6; and q in (III) is an integer from 0 to 6; X is

(VII)

$R^1$ is hydrogen or —COOH; $R^2$ is hydrogen, methyl or —CH$_2$COOH; Z is

(VIII)

R4 is alkyl, alkoxy, alkylamino, aryl, or hydroxyl (preferably R4 is alkyl); and r is an integer from about 5 to about 700.

The silicone graft polymers generally comprise from 0% to about 90% (preferably from about 5% to about 90%, more preferably from about 20% to about 90%) of monomer A, from about 0% to about 98% (preferably from about 7.5% to about 80%) of monomer B, and from about 1% to about 70% (preferably from about 1% to about 60%, most preferably from about 2% to about 50%) of monomer C. The combination of the A and B monomers preferably comprises from about 30.0% to about 99% (more preferably about 40% to about 98%, most preferably from about 40% to about 95%) of the polymer. The composition of any particular copolymer will help determine its formulational properties. In fact, by appropriate selection and combination of particular A, B and C components, the copolymer can be optimized for inclusion in specific vehicles. For example, polymers which are soluble or dispersible in an aqueous formulation preferably have the composition: from about 0% to about 70% (preferably from about 5% to about 70%) monomer A, from about 10% to about 98% (preferably from about 10% to about 80%, more preferably from about 10% to about 60%) monomer B, and from about 1% to about 50% monomer C.

Particularly preferred polymers for use in the present invention include the following (the weight percents below refer to the amount of reactants added in the polymerization reaction, not necessarily the amount in the finished polymer):

(A) acrylic acid/n-butylmethacrylate/ (polydimethylsiloxane (PDMS) macromer—3,000 molecular weight) (50/10/40 w/w/w), M.W.=20,000

(B) N,N-dimethylacrylamide/isobutyl methacrylate/ (PDMS macromer—2,000 molecular weight) (35/5/60 w/w/w), M.W.=10,000

(C) N,N-dimethylacrylamide/(PDMS macromer—4,000 molecular wt) (80/20 w/w), M.W.=20,000

(D) t-butylacrylate/acrylic acid/(PDMS macromer—3,000molecular wt) (40/40/20 w/w/w), M.W.=12,000

(E) t-butylacrylate/acrylic acid/(PDMS macromer - 12,000–14,000 molecular wt) (65/25/10 w/w/w), M.W.=80,000

(ii) Silicone Block Copolymers

Silicone block copolymers suitable for the present invention are exemplified by the formula

where n is an integer 1 or greater, that is, the block copolymers can be diblocks, multiblocks, or triblocks. These graft copolymers can be made by a number of methods known to those skilled in the art, including:

1. Formation of silicone/vinyl polymeric block copolymers using silicone macroinitiators. The polymers can be prepared according to the method described in *Macromolecular Design, Concepts and Practice*, M. K. Mishra, Ed, Polymer Frontiers International, Inc, 1994, Chapter 8.

2. Incorporation of silicone blocks using atom transfer radical polymerization. The polymers may be prepared according to the method described in "Development of Novel Attachable Initiator for Living Radical Polymerization and Synthesis of Polysiloxane Block Copolymer;" Yoshiki Nakagawa and Krzysztof Matyjaszewski; pages 270–271; Polymer Preprints, August 1996.

3. Cationic polymerization onto the ends of a silicone terminated with a cationic polymerization initiator. Such block copolymers are described in more detail in U.S. Pat. No. 4,659,777, to Riffle et al., issued Apr. 21, 1987, incorporated herein by reference.

Useful herein are silicone block copolymers comprising repeating block units of polysiloxanes.

Examples of silicone-containing block copolymers are found in U.S. Pat. No. 5,523,365, to Geck et al., issued Jun. 4, 1996; U.S. Pat. No. 4,689,289, to Crivello, issued Aug. 25, 1987; U.S. Pat. No. 4,584,356, to Crivello, issued Apr. 22, 1986; *Macromolecular Design, Concept & Practice*, Ed: M. K. Mishra, Polymer Frontiers International, Inc., Hopewell Jct., N.Y. (1994), and *Block Copolymers*, A. Noshay and J. E. McGrath, Academic Press, NY (1977), which are all incorporated by reference herein in their entirety. Other silicone block copolymers suitable for use herein are those described, along with methods of making them, in the above referenced and incorporated U.S. Pat. No. 5,658,577.

Silicone-containing block copolymers useful in the present invention include those which can be described by the formulas A—B, A—B—A, —(A—B)$_n$— and B—A—B wherein n is an integer of 2 or greater. A—B represents a diblock structure, A—B—A represents a triblock structure, and —(A—B)$_n$— represents a multiblock structure. The block copolymers can comprise mixtures of diblocks, triblocks, and higher multiblock combinations as well as small amounts of homopolymers.

The silicone block portion, B, can be represented by the following polymeric structure

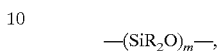

wherein each R is independently selected from the group consisting of hydrogen, hydroxyl, $C_1$–$C_6$ alkyl, $C_1$–$C_6$ alkoxy, $C_2$–$C_6$ alkylamino, styryl, phenyl, $C_1$–$C_6$ alkyl or alkoxy-substituted phenyl, preferably wherein R is methyl. In the preceding formula, m is an integer of about 10 or greater, m is an integer of about 40 or greater, more preferably of about 60 or greater, and most preferably of about 100 or greater.

The nonsilicone block, A, when formed by a synthetic process using radical polymerization, comprises monomers selected from the monomers as described above in reference to the A and B monomers for the silicone grafted copolymers. The block copolymers preferably contain up to about 80% (preferably from about 10% to about 70%) by weight of one or more polydimethyl siloxane blocks and one or more non-silicone blocks (preferably acrylates or vinyls).

Other silicone block copolymers useful are exemplified in U.S. Pat. No. 4,659,777, to Riffle and Yilgor, issued Apr. 21, 1987, assigned to Thoratec Laboratories. The non-silicone part of these blocks are poly(oxazoline). A preferred silicone block is an ABA where each A block is 3,000 M.W. poly(ethyl oxazoline) and the polydimethyl siloxane block M.W. is 3,000.

Additional silicone block copolymers suitable for use herein include those described in U.S. patent application Ser. No. 08/939,362, filed Sep. 29, 1997 in the names of Midha, Bolich and Jividen, Attorneys Docket No. 6591R, which is incorporated herein by reference in its entirety.

(iii) Sulfur-Linked Silicone Containing Copolymers

Also useful herein are sulfur-linked silicone containing copolymers, including block copolymers. As used herein in reference to silicone containing copolymers, the term "sulfur-linked" means that the copolymer contains a sulfur linkage (i.e., —S—), a disulfide linkage (i.e., —S—S—), or a sulfhydryl group (i.e., —SH).

These sulfur-linked silicone containing copolymers are represented by the following general formula:

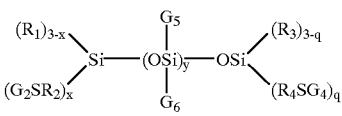

wherein $G_5$ independently represents monovalent moieties which can independently be the same or different selected from the group consisting of alkyl, aryl, alkaryl, alkoxy, alkylamino, fluoroalkyl, hydrogen, and —ZSA; A represents a vinyl polymeric segment consisting essentially of polymerized free radically polymerizable monomer, and Z is a divalent linking group. Useful divalent linking groups Z include but are not limited to the following: $C_1$ to $C_{10}$ alkylene, alkarylene, arylene, and alkoxyalkylene. Preferably, Z is selected from the group consisting of methylene and propylene for reasons of commercial availability.

$G_6$ represents monovalent moieties which can independently by the same or different selected from the group consisting of alkyl, aryl, alkaryl, alkoxy, alkylamino, fluoroalkyl, hydrogen, and —ZSA.

$G_2$ comprises A.

$G_4$ comprises A.

$R_1$ represents monovalent moieties which can independently be the same or different and are selected from the group consisting of alkyl, aryl, alkaryl, alkoxy, alkylamino, fluoroalkyl, hydrogen, and hydroxyl. Preferably, $R_1$ represents monovalent moieties which can independently be the same or different selected from the group consisting of $C_{1-4}$ alkyl and hydroxyl for reasons of commercial availability. Most preferably, $R_1$ is methyl.

$R_2$ can independently be the same or different and represents divalent linking groups. Suitable divalent lining groups include but are not limited to the following: $C_1$ to $C_{10}$ alkylene, arylene, alkarylene, and alkoxyalkylene. Preferably, $R_2$ is selected from the group consisting of $C_{1-3}$ alkylene and $C_7$–$C_{10}$ alkarylene due to ease of synthesis of the compound. Most preferably, $R_2$ is selected from the group consisting of —CH$_2$—, 1,3-propylene, and

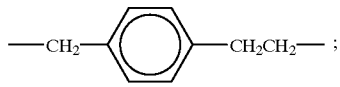

$R_3$ represents monovalent moieties which can independently be the same or different and are selected from the group consisting of alkyl, aryl, alkaryl, alkoxy, alkylamino, fluoroalkyl, hydrogen, and hydroxyl. Preferably, $R_3$ represents monovalent moieties which can independently be the same or different selected from the group consisting of $C_{1-4}$ alkyl and hydroxyl for reasons of commercial availability. Most preferably, $R_3$ is methyl.

$R_4$ can independently be the same or different and represents divalent lining groups. Suitable divalent linking groups include but are not limited to the following: $C_1$ to $C_{10}$ alkylene, arylene, alkarylene, and alkoxyalkylene. Preferably, $R_4$ is selected from the group consisting of $C_{1-3}$ alkylene and $C_7$–$C_{10}$ alkarylene for ease of synthesis. Most preferably, $R_4$ is selected from the group consisting of —CH$_2$—, 1,3-propylene, and

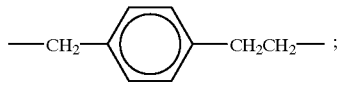

x is an integer of 0–3;

y is an integer of 20 or greater; preferably y is an integer ranging from about 20 to about 700, preferably from about 20 to about 200;

q is an integer of 0–3;

wherein at least one of the following is true:

q is an integer of at least 1;

x is an integer of at least 1;

$G_5$ comprises at least one —ZSA moiety;

$G_6$ comprises at least one —ZSA moiety.

As noted above, A is a vinyl polymeric segment formed from polymerized free radically polymerizable monomers. The selection of A is typically based upon the intended uses of the composition, and the properties the copolymer must possess in order to accomplish its intended purpose. If A comprises a block in the case of block copolymers, a polymer having AB and ABA architecture will be obtained depending upon whether a mercapto functional group —SH is attached to one or both terminal silicon atoms of the mercapto functional silicone compounds, respectively. The weight ratio of vinyl polymer block or segment, to silicone segment of the copolymer can vary. The preferred copolymers are those wherein the weight ratio of vinyl polymer segment to silicone segment ranges from about 98:2 to 50:50, in order that the copolymer possesses properties inherent to each of the different polymeric segments while retaining the overall polymer's solubility.

Sulfur linked silicone copolymers are described in more detail in U.S. Pat. No. 5,468,477, to Kumar et al., issued Nov. 21, 1995, and PCT Application No. WO 95/03776, assigned to 3M, published Feb. 9, 1995, which are incorporated by reference herein in their entirety. Additional patents with sulfur linked structures include U.S. Pat. No. 5,032,460, to Kanter et al, issued Jul. 16, 1991, assigned to 3M and U.S. Pat. No. 5,362,485, to Hayama et al, issued Nov. 8,1994, assigned to Mitsubishi Chem. Co.

Organopolysiloxane Emulsions

Preferred compositions of the present invention also contain an organopolysiloxane emulsion comprising polysiloxane particles dispersed in a suitable carrier, generally with the aid of a surfactant. The organopolysiloxane emulsion is generally an aqueous emulsion or microemulsion of an organopolysiloxane stabilized in the emulsion or microemulsion by one or more ionic or nonionic surfactants. Such emulsions and microemulsions can be prepared mechanically or by emulsion polymerization. Emulsions and microemulsions used in the present invention are preferably those prepared by emulsion polymerization.

The emulsion is preferably included in an amount such that the composition contains from about 0.01 to about 10% of the dispersed polysiloxane, more preferably about 0.05% to about 6%, most preferably about 0.1% to about 4%. Typically, the composition will include about 0.02 to about 50% of the emulsion.

Organopolysiloxane emulsions can be classified according to the average particle size, or diameter, of the dispersed organopolysiloxane in the emulsion. Emulsions prepared by emulsion polymerization generally comprise an organopolysiloxane as dispersed particles having a diameter of less than about 140 nanometers, more generally less than about 50 nanometers (often referred to as "microemulsions"). Fine emulsions are generally those containing particles of organopolysiloxane with a diameter of about 140–300 nanometers, while standard emulsions are generally those containing organosiloxane particles with a diameter greater than about 300 nanometers. Particle size of an emulsion can be determined by conventional methods, e.g., using a Leeds & Northrup Microtrac UPA particle sizer. Microemulsions are preferred for use herein.

The average particle size of the emulsion used in the present invention is preferably less than about 150 nanometers, more preferably less than about 100 nanometers, even more preferably less than about 80 nanometers, still more preferably less than about 60 nanometers, most preferably less than about 40 nanometers. Silicone emulsions having these particle sizes tend to be more stable and have better external appearance than those having larger particle sizes.

The organopolysiloxane in the emulsion can be a linear or branched chain siloxane fluid having a viscosity of about 20–3,000,000 mm$^2$/s (cs), preferably 300–300,000 cs, more preferably 350–200,000 cs, at 25° C.

Suitable organopolysiloxanes preferably contain the difunctional repeating "D" unit:

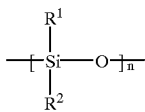

wherein n is greater than 1 and $R^1$ and $R^2$ are each independently $C_1$–$C_7$ alkyl or phenyl. A mixture of siloxanes may be used. Exemplary siloxanes include polydimethylsiloxane, polydiethylsiloxane, polymethylethylsiloxane, polymethylphenylsiloxane, and polydiphenylsiloxane. Siloxane polymers with dimethylsiloxane "D" units are preferred from an economic standpoint. However, $R^1$ and $R^2$ may independently be a functional group other than methyl, e.g., aminoalkyl, carboxyalkyl, haloalkyl, acrylate, acryloxy, acrylamide, mercaptoalkyl or vinyl.

The siloxane may be terminated with hydroxy groups, alkoxy groups such as methoxy, ethoxy, and propoxy, or trimethylsiloxy groups, preferably hydroxy or trimethylsiloxy.

The organopolysiloxane emulsions used herein can be produced by the emulsion polymerization of organosiloxane having a low degree of polymerization in a solvent comprising water. The organopolysiloxane is stabilized in the emulsion by a surfactant, e.g., a nonionic surfactant and an ionic surfactant. The degree of polymerization (DP) of the polysiloxane after emulsion polymerization is preferably in the range of from 3 to 5,000, more preferably in the range of from 10 to 3,000.

The emulsion can be prepared by the emulsion polymerization process described in EP 459500 (published Dec. 4, 1992), incorporated herein by reference. In that process, stable, oil free polysiloxane emulsions and microemulsions are prepared by mixing a cyclic siloxane, a nonionic surfactant, an ionic surfactant, water, and a condensation polymerization catalyst. The mixture is heated and agitated at polymerization reaction temperature until essentially all of the cyclic siloxane is reacted, and a stable, oil free emulsion or microemulsion is formed. The reaction mix, especially surfactant levels, and conditions are controlled in order to provide the desired organopolysiloxane particle size. The emulsions and microemulsions typically have a pH of about 3 to about 10 (e.g., 6–7.5), and contain about 10 to about 70% by weight siloxane polymer, preferably about 20 to about 60%, about 0% to about 30% by weight nonionic surfactant, about 0 to about 30% by weight ionic surfactant, preferably about 0 to about 20%, the balance being water. Preferred emulsions and methods of making them are further described in U.S. patent application Ser. No. 08/929,721, filed on Sep. 15, 1997 in the names of Ronald P. Gee and Judith M. Vincent, incorporated herein by reference in its entirety.

Emulsions can also be produced by the emulsion polymerization process described in EPA 0268982, published Jun. 6, 1988, assigned to Toray, incorporated herein by reference in its entirety. In this process, the emulsion is prepared by a process in which a crude emulsion, consisting of polysiloxane having a low degree of polymerization, a first surfactant (anionic, cationic, and nonionic surfactants), and water, is slowly dripped into an aqueous solution containing a catalytic quantity of a polymerization catalyst and a second surfactant which acts as an emulsifying agent (which may be the same as the first surfactant, however, the surfactants should be compatible in the reaction mixture considering the ionicity of the reaction mixture). The reaction mix and conditions are controlled to provide the desired organopolysiloxane particle size. Therefore, a dropwise addition of the crude emulsion into the aqueous solution of catalyst and surfactant of 30 minutes or longer is preferred in order to produce emulsions having smaller particle sizes. In addition, the quantity of surfactant used in the catalyst plus the surfactant aqueous solution is from about 5 to about 70 weight %, more preferably from about 25 to about 60 per 100 weight parts polysiloxane in the crude emulsion.

Any conventional nonionic surfactant can be used to prepare the emulsion. Exemplary types of nonionic surfactants include silicone polyethers, both grafted and linear block, ethoxylated fatty alcohols, ethoxylated alcohols, ethoxylated alkyl phenols, Isolaureth-6 (polyethylene glycol ether of branched chain aliphatic $C_{12}$ containing alcohols having the formula $C_{12}H_{25}(OCH_2CH_2)_6OH$), fatty acid alkanolamides, amine oxides, sorbitan derivatives (e.g., commercially available from ICI Americas, Inc., Wilmington, Del., under the tradenames SPAN and TWEEN), and propylene oxide-ethylene oxide block polymers (e.g., commercially available from BASF Corp., Parsippany, N.J. under the trademark PLURONIC). Ionic surfactants useful in preparing the emulsion include any conventional anionic surfactant such as sulfonic acids and their salt derivatives. Ionic surfactants also include any conventional cationic surfactant used in emulsion polymerization. Surfactants of these types are well known in the art and are commercially available from a number of sources. Specific examples of these surfactant types are also disclosed in the above referenced patent application Ser. No. 08/929,721.

The surfactant can be used in the form of a single type of surfactant (e.g., anionic, cationic or nonionic), or the surfactant can be used as a combination of two or more types provided that they are compatible with each other and the other components of the composition. Preferred combinations of surfactant types include the combination of two or more types of anionic surfactants, the combination of two or more types of nonionic surfactants, the combination of two or more types of cationic surfactants, the combination of two or more types of surfactants selected from both the anionic and nonionic surfactants; and the combination of two or more types of surfactants selected from both the cationic and nonionic surfactants.

The catalyst employed in the emulsion polymerization may be any catalyst capable of polymerizing cyclic siloxanes in the presence of water, including condensation polymerization catalysts capable of cleaving siloxane bonds. Exemplary catalysts include strong acids and strong bases, ionic surfactants such as dodecylbenzenesulfonic acid, phase transfer catalysts, and ion exchange resins where a catalyst is formed in situ. As will be understood by those skilled in the art, a given surfactant may also serve as the polymerization catalyst (e.g., alkylbenzenesulfonic acids, or quaternary ammonium hydroxides or salt thereof may function as both a surfactant and the polymerization catalyst).

A surfactant system, catalyst and resulting emulsion suitable for use in the compositions of the present invention can be selected by the skilled artisan considering the ionicity of the composition. In general, these materials are selected such that the total composition will be compatible.

Emulsions usefuil herein also include those produced by a mechanical emulsion process, although those produced by emulsion polymerization are preferred. In mechanical emulsions, the organopolysiloxane is generally present in the emulsion in the form of particles having a diameter greater than about 140 nanometer and less than about 350 nanometer, preferably less than about 300 nanometer. Mechanical emulsions can be prepared by known mechanical processes such as are described in U.S. Pat. No. 5,017,221 (May 21, 1991) and in EP 463431 (Jan. 2, 1992). Typical mechanical emulsions contain a trimethylsiloxy-terminated polydimethylsiloxane stabilized by a nonionic surfactant. According to such mechanical processes, water, one or more nonionic surfactants, and the organopolysiloxane are mixed together, and homogenized using a laboratory homogenizer or other device for applying vigorous agitation. These mechanical emulsions typically have a pH of 7–9.5, and contain 10–80% by weight of the siloxane, preferably 20–60%, 0.01–15% by weight of the nonionic surfactant(s), the balance being water.

Organopolysiloxane emulsions are available from a number of commercial sources. The following organopolysiloxane emulsions are manufactured by Dow Corning of Midland, Mich.

Emulsions containing dimethicone copolyol:

| Emulsion Trade Name | Si Type | Internal phase viscosity (cps) | Surfactant | Si particle size, nm |
|---|---|---|---|---|
| DC 2-5791 - LP | Dimethylsiloxanol, Dimethyl cyclosiloxane | 70–90M | Triethanolamine dodecylbenzene sulfonate, Polyethylene oxide lauryl ether | 123 |
| DC 2-5791 - MP | Dimethylsiloxanol, Dimethyl cyclosiloxane | 70–90M | Triethanolamine dodecylbenzene sulfonate, Polyethylene oxide lauryl ether | 93 |
| DC 2-5791 | Dimethylsiloxanol, Dimethyl cyclosiloxane | 70–90M | Triethanolamine dodecylbenzene sulfonate, Polyethylene oxide lauryl ether | <50 |
| DC 2-5791 - sp | Dimethylsiloxanol, Dimethyl cyclosiloxane | 70–90M | Triethanolamine dodecylbenzene sulfonate, Polyethylene oxide lauryl ether | <40 |
| DC 2-5932 | Dimethylsiloxanol, Dimethyl cyclosiloxane | 1–2M | Cetrimonium Chloride, Trideceth-12 | <30 |

| Emulsion Trade Name | Si Type | Internal phase viscosity (cps) | Surfactant | Si particle size, nm |
|---|---|---|---|---|
| DC 2-1470 - LP | Dimethylsiloxanol, Dimethyl cyclosiloxane | 15–20M | Triethanolamine dodecylbenzene sulfonate, Polyethylene oxide lauryl ether | 124 |
| DC 2-1470 - MP | Dimethylsiloxanol, Dimethyl cyclosiloxane | 4–8M | Triethanolamine dodecylbenzene sulfonate, Polyethylene oxide lauryl ether | 94 |
| DC 2 - 1716 MEM | Dimethylsiloxanol with methyl silsequioxane, Octamethyl cyclotretrasiloxane | 10–30M | Cetrimonium Chloride, Trideceth-12 | 50–80 |
| DC 2-8937 | Mercapto-siloxane | | Cetrimonium Chloride, Trideceth-12 | 50–70 |
| DC 2-1470 | Dimethylsiloxanol, Dimethyl cyclosiloxane | 15–20M | Triethanolamine dodecylbenzene sulfonate, Polyethylene oxide lauryl ether | <50 |
| DC 2-1845 | Dimethylsiloxanol, Dimethyl cyclosiloxane | 4–8M | Triethanolamine dodecylbenzene sulfonate, Polyethylene oxide lauryl ether | <40 |
| DC 2-1845 - HV | Dimethylsiloxanol, Dimethyl cyclosiloxane | 60–70M | Triethanolamine dodecylbenzene | <35 |

-continued

| Emulsion Trade Name | Si Type | Internal phase viscosity (cps) | Surfactant | Si particle size, nm |
|---|---|---|---|---|
| DC 2-1550 | Dimethylsiloxanol, Dimethyl cyclosiloxane | 100–600M | sulfonate, Polyethylene oxide lauryl ether Triethanolamine dodecylbenzene sulfonate, Polyethylene oxide lauryl ether | ≦50 |
| DC 2-1281 | Dimethylsiloxanol, Dimethyl cyclosiloxane | 1–2M | Cetrimonium Chloride, Trideceth-12 | <30 |
| DC 2-8194 | Dimethyl, aminomethyl propyl siloxane | 4–6M | Cetrimonium Chloride, Trideceth-12 | ≦30 |

It is generally preferred to use emulsions having lower particle sizes as described above.

Where the silicone functional polymer is an anionic acrylate polymer or the composition contains an anionic acrylate hair styling polymer, DC-2-1845 and DC 2-5791 are preferred emulsions. Where either of the foregoing polymers is a cationic polymer comprising nitrogen, the DC-2-8194, DC-2-1281 and/or DC 2-5932 emulsions are preferred.

Carrier

The compositions of the invention also comprise a carrier for the silicone functional polymer and the organopolysiloxane emulsion. Suitable carriers are those in which the silicone functional polymer is soluble or dispersible, preferably soluble or microdispersible, and in which the organopolysiloxane is dispersible. Choice of an appropriate carrier will also depend on the particular end use and product form contemplated (e.g., the hair styling polymer to be used, and the product form, e.g., for hair styling compositions such as hair spray, mousse, tonic, lotion or gel). Preferred carriers are those which are suitable for application to the hair, skin, or nails.

The carrier is present at from about 0.5% to about 99.5%, preferably from about 5% to about 99.5%, most preferably from about 50% to about 95%, of the composition.

The compositions of the present invention comprise one or more suitable solvents for the silicone functional polymer. Preferred solvent systems are those which form a homogeneous solution or dispersion (preferably microdispersion) with the silicone functional polymer in the weight ratios used in the composition. Preferred solvent systems are those which form a substantially clear to translucent solution or dispersion (preferably microdispersion) with the silicone functional polymer in the weight ratios used in the composition.

Preferred solvents include those selected from the group consisting of water; water soluble organic solvents; organic solvents which are strongly to moderately strong in hydrogen-bonding parameter; and mixtures thereof; wherein the solvent is other than $C_1$–$C_3$ monohydric alcohol, $C_1$–$C_3$ ketone and $C_1$–$C_3$ ether. Water is a preferred solvent. At least about 0.5%, preferably at least about 1%, of this type of solvent is used in the composition.

Exemplary water soluble organic solvents other than $C_1$–$C_3$ monohydric alcohols, ketones and ethers include propylene glycol, glycerine, phenoxyethanol, dipropylene glycol, sugars, and mixtures thereof.

Solvents which are moderately strong to strong in hydrogen-bonding parameter other than $C_1$–$C_3$ monohydric alcohols, ketones and ethers include esters, ethers, ketones, glycol monoethers (moderately H-bonded) and alcohols, amines, acids, amides and aldehydes (strongly H-bonded). A description and examples of solvents of this type are disclosed in Polymer Handbook, 2d. Ed., J. Brandrup and E. H. Immergut, Editors, John Wiley & Sons, N.Y., 1975, Section IV, page 337–348 (Table 2). Preferred solvents of this type are dibutyl phthalate, propylene carbonate, propylene glycol monomethyl ether, methyl acetate, methyl proprionate and mixtures thereof. Propylene glycol monomethyl ether, methyl acetate, methyl proprionate and mixtures thereof are preferred; methyl acetate is most preferred.

Other solvents suitable for use herein are water soluble, organic volatile solvents selected from $C_1$–$C_3$ monohydric alcohols, $C_1$–$C_3$ ketones, $C_1$–$C_3$ ethers, and mixtures thereof, monohydric alcohols being preferred. Preferred solvents of this type are methylal, ethanol, n-propanol, isopropanol, acetone and mixtures thereof. More preferred are ethanol, n-propanol, isopropanol, and mixtures thereof.

In a preferred embodiment, the carrier comprises (i) a solvent selected from the group consisting of water; water soluble organic solvents; organic solvents which are strongly to moderately strong in hydrogen-bonding parameter; and mixtures thereof, wherein the solvent is other than $C_1$–$C_3$ monohydric alcohol, $C_1$–$C_3$ ketone and $C_1$–$C_3$ ether; (ii) a solvent selected from the groups consisting of $C_1$–$C_3$ monohydric alcohols, $C_1$–$C_3$ ketones, $C_1$–$C_3$ ethers, and mixtures thereof, and (iii) mixtures thereof, preferably a mixture thereof. Especially preferred are a mixture of water and $C_1$–$C_3$ monohydric alcohol, e.g., water-ethanol or water-isopropanol-ethanol. Another particularly preferred solvent system comprises one or more of propylene glycol monomethyl ether, methyl acetate, and methyl proprionate, preferably methyl acetate, optionally with one or more of water or a $C_1$–$C_3$ monohydric alcohol.

The carrier may include other solvents, e.g., hydrocarbons (such as isobutane, hexane, decene, acetone), halogenated hydrocarbons (such as Freon), linalool, volatile silicon derivatives, especially siloxanes (such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), and mixtures thereof.

Solvents used in admixture may be miscible or immiscible with each other. However, in the final composition such solvents should be compatible with each other and other components in the composition such that solids do not precipitate.

Reduced "volatile organic compound" or "VOC" compositions may be desirable. In this regard, "VOC" refers to those organic compounds that contain less than 12 carbon atoms or have a vapor pressure greater than about 0.1 mm of mercury. For example, the composition may have, as initially applied, a total VOC content of about 95% or less, about 80% or less, about 55% or less (e.g., in preferred hairsprays), about 16% or less (e.g., in preferred mousses), or about 6% or less (e.g., in preferred gels). The VOC may be based on actual VOC content, or the VOC which is delivered upon initial dispensing from a package.

Where the composition comprises a silicone graft hair styling copolymer, the compositions hereof may contain a volatile, nonpolar, branched chain hydrocarbon, which acts as a solvent for the silicone portion of the silicone grafted copolymer. When used, the branched chain hydrocarbon solvent hereof is present at a level of from about 0.01% to about 15%, preferably from about 0.05% to about 10%, more preferably from about 0.1% to about 8%, by weight of the composition.

The branched chain hydrocarbon solvent is characterized by a boiling point of at least about 105° C., preferably at least about 110° C., more preferably at least about 125° C., most preferably at least about 150° C. The boiling point is also generally about 260° C. or less, preferably about 200° C. or less. The hydrocarbon chosen should also be safe for topical application to the hair and skin.

The branched chain hydrocarbon solvents are described in detail in U.S. Pat. No. 5,565,193 and are hereby incorporated by reference. The solvent includes those selected from the group consisting of $C_{10}$–$C_{14}$ branched chain hydrocarbons, and mixtures thereof, preferably $C_{11}$–$C_{13}$ branched chain hydrocarbons, more preferably $C_{12}$ branched chain hydrocarbons. Saturated hydrocarbons are preferred, although it isn't necessarily intended to exclude unsaturated hydrocarbons.

Examples of suitable nonpolar solvents include isoparaffins of the above chain sizes. Isoparaffins are commercially available from Exxon Chemical Co. Examples include Isopar™ G ($C_{10}$–$C_{11}$ isoparaffins), Isopar™ H and K ($C_{11}$–$C_{12}$ isoparaffins), and Isopar™ L ($C_{11}$–$C_{13}$ isoparaffins). The most preferred nonpolar solvent are $C_{12}$ branched chain hydrocarbons, especially isododecane. Isododecane is commercially available from Preperse, Inc. (South Plainfield, N.J., USA) as Permethyl™ 99A.

The solubility of the silicone portion of the hair styling polymer can be easily determined by verifying whether a silicone polymer of the same composition and molecular weight as that in the hair styling polymer is soluble in the nonpolar hydrocarbon solvent. In general, the silicone polymer should be soluble at 25° C. at a concentration of 0.1% by weight of the hydrocarbon solvent, preferably at 1%, more preferably at 5%, most preferably at 15%.

The nonpolar hydrocarbon solvent, however, is insoluble in the polar solvents of the composition. This is determined in the absence of the hair styling polymer, or other emulsifying agents, and can easily be verified by observing whether the polar and nonpolar solvents form separate phases after being mixed together.

Without intending to be necessarily limited by any particular theory, it is believed that the nonpolar hydrocarbon solvent solubilizes the silicone portion of the hair styling polymer. This is believed to aid in obtaining a smoother polymer film upon drying.

The carrier may also comprise conventional components such as are known in the art suitable for a given product form.

Optional Components

Compositions of the invention may contain a variety of other ingredients such as are conventionally used in a given product form. Compositions of the present invention are especially usefhll in preparing personal care products, household care products, automotive care products, and coating products. In the personal care area, compositions hereof include those in the form of hair care, skin care (including underarm), and nail care compositions. Specific examples include hair styling compositions such as hairsprays, mousses, gels, lotions, creams, hair dressings, volumizing sprays, spray-on products such as spray-on gels, heat protectant sprays, spritzes, pomades, and hair tonics, as well as nail polishes, nail polish removers, wet wipe lotions, antibacterial lotion (e.g., for hand wipes), cleansing towellettes, hand sanitizers, make-up removers, skin toners, shampoos (including 2-in-1, combined shampoos and conditioners), hair conditioners, soaps, lotions, creams, fragrances (e.g., colognes), skin cleansers, afterbath splashes, shaving creams, aftershave stick lotions, insect repellants, antiperspirants, deodorants, anti-acne products, lipsticks, foundations, mascaras, eye make-ups, sunscreens (including spray-on sunscreens), and the like. The compositions may be aerosol or non-aerosol. Hair styling compositions such as those listed above are described, for example in California Code of Regulations, Regulation for Reducing Volatile Organic Compound Emissions from Consumer Products, Amendment 2, Consumer Products, Sections 94507-94717, Title 17, filed Sep. 19, 1991 and effective Oct. 21, 1991; and Jellinek, J. S. Formulation and Function of Cosmetics, Wiley-Interscience (1970); each incorporated herein by reference.

For example, personal care compositions of the present invention can contain a wide variety of other optional ingredients that are suitable for application to human hair, skin, or nails, including among them any of the types of ingredients known in the art for use in hair, skin, or nail care compositions, especially hair setting compositions like hair spray compositions, mousses, gels and tonics. Generally, such other adjuvants collectively comprise from about 0.05% to about 20% by weight and preferably from about 0.1% to about 10%, by weight of the compositions. Such conventional optional adjuvants are well known to those skilled in the art and include, but are not limited to, hair styling polymers, plasticizers, surfactants (which may be anionic, cationic, amphoteric or nonionic), neutralizing agents, propellants, hair conditioning agents (including polymeric and non-polymeric agents, e.g., silicone fluids, fatty esters, fatty alcohols, long chain hydrocarbons, isobutene, cationic surfactants, etc.), emollients, lubricants and penetrants such as various lanolin compounds, vitamins, proteins, preservatives, dyes, tints, bleaches, reducing agents and other colorants, sunscreens, thickening agents (e.g., polymeric thickeners, such as xanthan gum), physiologically active compounds for treating the hair, skin or nails (e.g., anti-dandruff actives, hair growth actives), and perfume.

Non-exclusive examples of certain types of optional components are provided below.

a) Hair Styling Polymers

Preferred compositions are hair styling compositions containing a hair styling polymer. As will be understood in the art, the silicone functional polymers described above may provide hair styling benefits. In addition to the silicone functional polymers described above, the compositions of the present invention may comprise a or another hair styling polymer. Suitable hair styling polymers include both silicone containing hair styling polymers such as described above (provided they provide styling properties, e.g., have a molecular weight sufficient to provide styling properties), and non-silicone containing hair styling polymers. Suitable hair styling polymers are those which are soluble or microdispersible in the primary solvent system described herein in the weight ratios employed in the composition. Solubility is determined as described in reference to the silicone functional polymer.

When used, the silicone-containing hair styling polymers are preferably present in a combined amount of from about 0.01% to about 20%, more preferably from about 0.1% to about 15%, and most preferably from about 1% to about 10% by weight of composition. When the hair styling polymer is a silicone graft copolymer, precopolymers include:

acrylic acid/n-butylmethacrylate/(polydimethylsiloxane (PDMS) macromer—20,000 molecular weight) (10/70/20 w/w/w) (polymer molecular weight=80–200M)

N,N-dimethylacrylamide/isobutyl methacrylate/(PDMS macromer—20,000 molecular weight) (20/60/20 w/w/w) (polymer molecular weight=50–300M)

N,N-dimethylacrylamide/(PDMS macromer—20,000 molecular wt) (80/20 w/w)(polymer molecular weight= 50–500M)

t-butylacrylate/acrylic acid/(PDMS macromer—12,000–14,000 molecular wt) (60/20/20 w/w/w)(polymer molecular weight=120–150M)

t-butylacrylate/acrylic acid/(PDMS macromer—12,000–14,000 molecular wt) (65/25/10 w/w/w)(polymer molecular weight=100–140M)

t-butylacrylate/acrylic acid/(PDMS macromer—10,000–15,000 molecular wt) (60/20/20 w/w/w)(polymer molecular weight=50–160M)

t-butylacrylate/methacrylic acid/(PDMS macromer—12,000–14,000 molecular wt) (60/20/20 w/w/w)(polymer molecular weight=50–160M)

t-butylacrylate/acrylic acid/(PDMS macromer—2,000–5,000 molecular wt) (60/20/20 w/w/w)(polymer molecular weight=50–150M)

quaternized dimethylaminoethyl methacrylate/isobutyl methacrylate/(PDMS macromer—10,000–15,000 molecular wt) (60/20/20 w/w/w)(polymer molecular weight=90–120 M)

Non-silicone-containing hair styling polymers include nonionic, anionic, cationic, and amphoteric polymers, and mixtures thereof. When used, the non-silicone-containing hair styling polymers are preferably present in a combined amount of from about 0.01% to about 20%, more preferably from about 0.1% to about 15%, and most preferably from about 0.5% to about 10% by weight of composition.

Suitable cationic polymers include Polyquaternium-4 (Celquat H-100; L200—supplier National Starch); Polyquaternium-10 (Celquat SC-240C; SC-230 M—supplier National Starch); (UCARE polymer series—JR-125, JR-400, LR-400, LR-30M, LK, supplier Amerchol ); Polyquaternium-11 (Gafquat 734; 755N—supplier ISP); Polyquaternium-16 (Luviquat FC 370; FC550; FC905; HM-552 supplier by BASF); PVP/Dimethylaminoethylmethacrylate (Copolymer 845; 937; 958—ISP supplier); Vinyl Caprolactam/PVP/Dimethylaminoethyl Methacrylate copolymer (Gaffix VC-713; H$_2$OLD EP-I—supplier ISP); Chitosan (Kytamer L; Kytamer PC—supplier Amerchol); Polyquaternium-7 (Merquat 550—supplier Calgon); Polyquaternium-18 (Mirapol AZ-I supplied by Rhône-Poulenc); Polyquaternium-24 (Quatrisoft Polymer LM-200—supplier Amerchol); Polyquaternium-28 (Gafquat HS-100—supplier ISP); Polyquaternium-46 (Luviquat Hold—supplier BASF); and Chitosan Glycolate (Hydagen CMF; CMFP—supplier Henkel); Hydroxyethyl Cetyldimonium Phosphate (Luviquat Mono CP—supplier BASF); and Guar Hydroxylpropyl Trimonium Chloride (Jaguar C series -13 S, -14S, -17, 162,-2000, Hi-CARE 1000—supplier Rhône-Poulenc).

Preferred cationic polymers are Polyquaternium-4; Polyquaternium-10; Polyquaternium-11; Polyquaternium-16; PVP/Dimethylaminoethylmethacrylate; Vinyl Caprolactam/PVP/Dimethylaminoethyl Methacrylate copolymer; and Chitosan.

Suitable amphoteric polymers include Octylacrylmide/Acrylates/Butylaminoethyl Methacrylate Copolymer (Amphomer 28-4910, Amphomer LV-71 28-4971, Lovocryl-47 28-4947 - National Starch supplier), and Methacryloyl ethyl betaine/methacrylates copolymer (Diaformer series supplier Mitsubishi). Preferred are Octylacrylmide/Acrylates/Butylaminoethyl Methacrylate Copolymer.

Especially preferred polymers for relatively low alcohol systems, e.g., less than about 55% alcohol, are those which are partially zwitterionic in that they always possess a positive charge over a broad range of pH but contain acidic groups which are only negatively charged at basic pH. Therefore the polymer is positively charged at lower pH and neutral (have both negative and positive charge) at higher pHs. Zwitterionic polymers useful herein include Polyquaternium-47 (Merquat 2001—supplier Calgon); Carboxyl Butyl Chitosan (Chitolam NB/101—marketed by Pilot Chemical Company, developed by Lamberti); and Dicarboxyethyl Chitosan available from Amerchol as an experimental sample.

Useful nonionic polymers include PVP or Polyvinylpyrrolidone (PVP K-15, K-30, K-60, K-90, K-120—supplier ISP) (Luviskol K series 12, 17, 30, 60, 80, & 90—supplier BASF); PVP/VA (PVP/VA series S-630; 735, 635, 535, 335, 235—supplier ISP)(Luviskol VA); PVP/DMAPA acrylates copolymer (Styleze CC-10—supplier ISP); PVP/VA/Vinyl Propionate copolymer (Luviskol VAP 343 E, VAP 343 I, VAP 343 PM—supplier BASF); Hydroxylethyl Cellulose (Cellosize HEC—supplier Amerchol); and Hydroxylpropyl Guar Gum (Jaguar HP series -8, -60, -105, -120 —supplier Rhône-Poulenc).

Preferred nonionic polymers are PVP or Polyvinylpyrrolidone; PVP/VA; PVP/DMAPA acrylates copolymer; and Hydroxylpropyl Guar Gum.

Anionic polymers suitable for use herein include VA/Crotonates/Vinyl Neodecanonate Copolymer (Resyn 28-2930—National Starch supplier); Butyl Ester of PVM/MA (Gantrez A-425; ES-425; ES-435—supplier ISP); Ethyl Ester of PVM/MA (Gantrez ES-225; SP-215—supplier ISP); Acrylates/acrylamide copolymer (Luvimer 100P; Lumiver Low VOC, supplier BASF); Methacrylate Copolymer (Balance 0/55—National Starch supplier); Vinyl Acetate/Crotonic Acid copolymer (Luviset CA 66—supplier BASF); Isopropyl Ester of PVM/MA Copolymer (Gantrez ES-335—supplier ISP); Acrylates Copolymer; Methacrylates/acrylates copolymer/amine salt (Diahold polymers—supplier Mitsubishi); 2-Butenedioic Acid (Z)-, Monoethyl Ester, Polymer with Methoxyethene (Omnirez 2000); VA/Butyl maleate/Isobornyl Acrylate (Advantage Plus terpolymer—supplier ISP); Acrylates Copolymer (Amerhold DR-25—supplier Amerchol); Acrylates/Hydroxyesteracrylates Copolymer (Acudyne 255 supplier Rohm & Haas); vinyl Acetate/Crotonic Acid/Vinyl Propionate copolymer (Luviset CAP—supplier BASF); PVP/Acrylates copolymer (Luviflex VBM 35—supplier BASF); Diglycol/CHDM/Isophthalates/SIP Copolymer (Eastman AQ 48, AQ 55—supplier Eastman Chemicals); Acrylates/Octacrylamide Copolymer (Versatyl-42 or Amphomer HC—National Starch supplier); t-butyl acrylate/acrylic acid copolymer 75/25 (Mitsubishi Chemical Corp.); Acrylates Copolymer (Aculyn 33—supplier Rohm & Haas) and Acrylates/Steareth-20 Methacrylate Copolymer (Aculyn 22—Supplier Rohm & Haas) and Carbomer (supplier B.F. Goodrich).

Preferred anionic polymers are VA/Crotonates/Vinyl Neodecanonate Copolymer; Butyl Ester of PVM/MA; Ethyl Ester of PVM/MA; Acrylates/acrylamide copolymer; Methacrylate Copolymer; and Vinyl Acetate/Crotonic Acid copolymer.

b) Plasticizers

The compositions hereof may contain a plasticizer, e.g., for a hair styling polymer which may be present in the composition. Any plasticizer suitable for use in hair care products or for topical application to the hair, skin or nails can be used. A wide variety of plasticizers are known in the art. These include glycerine, diisobutyl adipate, butyl stearate, propylene glycol, diethylene glycol, other glycols, tri-$C_2$–$C_8$ alkyl citrates, including triethyl citrate and analogs of triethyl citrate.

In hair styling compositions, plasticizers are typically used at levels of from about 0.01% to about 200%, by weight of the composition, preferably from about 0.05% to about 100%, more preferably from about 0.05% to about 50%, by weight of hair styling polymer.

c) Surfactants

The personal care compositions can contain one or more surfactants, e.g., for emulsifying hydrophobic components which may be present in the composition. Surfactants are preferred for use in mousse products. Generally, if used such surfactants will be used at a total level of from about 0.01% to about 10%, preferably from about 0.01% to about 5% and more preferably from about 0.01% to about 3%, by weight of the composition. A wide variety of surfactants can be used, including anionic, cationic, amphoteric, and zwitterionic surfactants.

Anionic surfactants include, for example: alkyl and alkenyl sulfates; alkyl and alkenyl ethoxylated sulfates; (preferably having an average degree of ethoxylation of 1 to 10), succinamate surfactants, such as alkylsulfosuccinamates and dialkyl esters of sulfosuccinic acid; neutralized fatty acid esters of isethionic acid; and alkyl and alkenyl sulfonates, including, for example, olefin sulfonates and beta-alkoxy alkane sulfonates. Preferred are alkyl and alkenyl sulfates and alkyl and alkenyl ethoxylated sulfates such as the sodium and ammonium salts of $C_{12}$–$C_{18}$ sulfates and ethoxylated sulfates with a degree of ethoxylation of from 1 to about 6, preferably from 1 to about 4, e.g., lauryl sulfate and laureth (3.0) sulfate.

Amphoteric surfactants include those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, N-alkyltaurines such as the one prepared by reacting dodecylamine with sodium isethionate according to the teaching of U.S. Pat. No. 2,658,072, N-higher allyl aspartic acids such as those produced according to the teaching of U.S. Pat. No. 2,438,091, and the products sold under the trade name "Miranol" and described in U.S. Pat. No. 2,528,378. Others include alkyl, preferably $C_6$–$C_{22}$ and most preferably $C_8$–$C_{12}$, amphoglycinates; alkyl, preferably $C_6$–$C_{22}$ and most preferably $C_8$–$C_{12}$, amphopropionates; and mixtures thereof.

Suitable zwitterionic surfactants for use in the present compositions can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

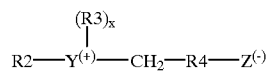

wherein R2 contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; x is 1 when Y is sulfur or phosphorus, 1 or 2 when Y is nitrogen; R4 is an alkylene or hydroxyalkylene of from 1 to about 4 carbon atoms and Z is a radical selected from the group consisting of carboxylate, sulfonate, sulfate, phosphonate, and phosphate groups. Classes of zwitterionics include alkyl amino sulfonates, alkyl betaines, and alkyl amido betaines.

Cationic surfactants useful in compositions of the present invention contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

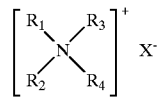

wherein $R_1$ is an aliphatic group of from 1 to 22 carbon atoms, or an aromatic, aryl or alkylaryl group having from 12 to 22 carbon atoms; $R_2$ is an aliphatic group having from 1 to 22 carbon atoms; $R_3$ and $R_4$ are each alkyl groups having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amido groups. Other quaternary ammonium salts useful herein are diquaternary ammonium salts.

Salts of primary, secondary and tertiary fatty amines are also suitable cationic surfactants for use herein. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidyl-behenylamine. Cationic amine surfactants included among those useful in the present invention are disclosed in U.S. Pat. No. 4,275,055, Nachtigal, et al., issued Jun. 23, 1981 (incorporated by reference herein).

Suitable cationic surfactant salts include the halogen, acetate, phosphate, nitrate, citrate, lactate and alkyl sulfate salts.

Nonionic surfactants can also be included in the compositions hereof. Nonionic surfactants include polyethylene oxide condensates of alkyl phenols (preferably $C_6$–$C_{12}$ alkyl, with a degree of ethoxylation of about 1 to about 6), condensation products of ethylene oxide with the reaction product of propylene oxide and ethylene diamine, condensation products of aliphatic alcohols with ethylene oxide, long chain (i.e., typically $C_{12}$–$C_{22}$) tertiary amine oxides, long chain tertiary phosphine oxides, dialkyl sulfoxides containing one long chain alkyl or hydroxy alkyl radical and one short chain (preferably $C_1$–$C_3$) radical, silicone copolyols, and $C_1$–$C_4$ alkanol amides of acids having a $C_8$–$C_{22}$ acyl moiety. Preferred nonionic surfactants are $C_1$–$C_4$ alkanol amides of acids having a $C_8$–$C_{22}$ acyl moiety (e.g., Lauramide DEA), and polyoxyethylene glycol stearyl ethers, and mixtures thereof. Specific examples which are preferred are Lauramide DEA, Steareth-21, Steareth-2, and Sodium Cocoyl Isethionate.

Additional surfactants suitable for use herein include those described in reference to the emulsion.

d) Neutralizing Agents

Neutralizing agents may also be used in the compositions herein. For example, when the personal care composition comprises a hair styling polymer which has acidic functionalities, such as carboxyl groups, are preferably used in at least partially neutralized form to promote solubility/dispersibility of the polymer. In addition, use of the neutralized form aids in the ability of the dried hair styling compositions to be removed from the hair by shampooing. The degree of neutralization must balance shampoo removability versus humidity resistance. Neutralization levels in excess of what is required for shampoo removability will result in excessively sticky products that will not hold as well in high humidity. When available acidic monomers are neutralized, it is preferred that from about 5% to 60%, more preferably from about 10% to about 40%, and even more preferably from about 12% to about 30% of the polymer (on a total polymer weight basis) be neutralized. The optimal level of neutralization for a specific polymer will depend on the polarity of the monomers selected, the specific ratios of the monomers to each other, and the percentage of acidic monomers. The level of base needed to neutralize the acid groups in a polymer for a specific % neutralization of the polymer may be calculated from the following equation:

$$\% \text{ Base in} = A \times (B/100) \times (C/D) \text{ composition}$$

A=% Polymer in composition
B=% of polymer to be neutralized (assuming acid groups are available)
C=MW of Base
D=MW of Acid monomer Any conventionally used base, including organic or inorganic (metallic or other) bases, can be used for neutralization of the polymers. Metallic bases are particularly usefull in the present compositions. Hydroxides, where the cation is ammonium, an alkali metal or an alkaline earth metal, are suitable neutralizers for use in the present compositions. Preferred inorganic neutralizing agents for use in the compositions of the present invention are potassium hydroxide and sodium hydroxide. For silicone grafted hair styling polymers in compositions with water levels >30%, sodium hydroxide is the most preferred inorganic base. Examples of other suitable neutralizing agents which may be included in the personal care compositions of the present invention include amines, especially amino alcohols such as 2-amino-2-methyl-1,3-propanediol (AMPD), 2-amino-2-ethyl-1,3-propanediol (AEPD), 2-mino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), triisopropanolamine (TIPA), dimethyl laurylamine (DML), dimethyl myristalamine (DMM) and dimethyl stearamine (DMS) For silicone grafted polymers, particularly useful neutralizing agents are dimethyl myristalamine, dimethyl laurylamine, and mixtures thereof.

Hair styling or other polymers having basic functionalities, e.g., amino groups, are preferably at least partially neutralized with an acid, e.g., hydrochloric acid.

Neutralization can be accomplished by techniques well known in the art, and before or after polymerization of the monomers comprising the hair styling or other polymer.

e) Hair Conditioning Polymers

The compositions of the invention may include a hair conditioning polymer for purposes of improved wet combing, dry combing and/or improved manageability (e.g., frizz or static control). Hair conditioning polymers are typically used at a level of from about 0.001 to about 6%, preferably about 0.01 to about 5%, of the composition.

Cationic and zwitterionic hair conditioning polymers are preferred. Suitable hair conditioning polymers include cationic polymers having a weight average molecular weight of from about 5,000 to about 10 million, and will generally have cationic nitrogen-containing moieties such as quaternary ammonium or cationic amino moieties, and mixtures thereof. Cationic charge density should be at least about 0.1 meq/gram, preferably less than about 3.0 meq/gram, which can be determined according to the well known Kjeldahl Method. Those skilled in the art will recognize that the charge density of amino-containing polymers can vary depending upon pH and the isoelectric point of the amino groups. The charge density should be within the above limits at the pH of intended use. Any anionic counterions can be utilized for the cationic polymers so long as they are compatible.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in *International Cosmetic Ingredient Dictionary*, Sixth Edition, 1995, which is incorporated by reference herein in its entirety.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of poly-vinyl acetate), maleic anhydride, propylene glycol, and ethylene glycol. The cationic polymers are described in detail in U.S. Pat. No. 4,733,677 which is hereby incorporated by reference to further describe the cationic polymers used for conditioning purposes.

The cationic amines can be primary, secondary, or tertiary amines, depending upon the particular species and the pH of the composition. In general, secondary and tertiary amines, especially tertiary amines, are preferred. The cationic polymers can comprise mixtures of monomer units derived from amine- and/or quaternary ammonium-substituted monomer and/or compatible spacer monomers.

Other cationic polymers that can be used include polysaccharide polymers, such as cationic cellulose derivatives, cationic starch derivative, and cationic guar gum derivatives. Other materials include quaternary nitrogen-containing cellulose ethers as described in U.S. Pat. No. 3,962,418, and copolymers of etherified cellulose and starch as described in U.S. Pat. No. 3,958,581, which descriptions are incorporated herein by reference.

Where the composition comprises a neutralized, anionic hair styling polymer and a zwitterionic hair conditioning polymer, the pH of the zwitterion is preferably adjusted to that of the neutralized hair styling polymer prior to combination therewith. Such neutralization can be achieved by conventional methods using any conventional pH adjusting agent.

f) Propellants

Propellants may also be used in the compositions herein. For example, hair styling or other compositions according to the present invention which are to be dispensed from a pressurized aerosol container (e.g., certain hair sprays and mousses), generally comprise a propellant which consists of one or more of the conventionally-known aerosol propellants to propel the compositions. A suitable propellant for use can be any gas conventionally used for aerosol containers, preferably a liquifiable gas. Suitable propellants for use are volatile hydrocarbon propellants which can include liquified lower hydrocarbons of 3 to 4 carbon atoms such as propane, butane and isobutane. Other suitable propellants are hydrofluorocarbons such as 1,2-difluoroethane (Hydrofluorocarbon 152A) supplied as Dymel 152A by DuPont. Other examples of propellants are dimethylether, nitrogen, carbon dioxide, nitrous oxide, and atmospheric gas. For hair sprays and mousses, the selection of appropriate hydrocarbons is made to provide a stable system giving the desired spray/foam quality.

The aerosol propellant may be mixed with the present compositions and the amount of propellant to be mixed is governed by normal factors well known in the aerosol art. Generally, for liquifiable propellants, the level of propellant is from about 1% to about 60% by weight of the total composition. For hair sprays, the propellant level is from about 10% to about 60% by weight of the total composition, preferably from about 15% to about 50% by weight of the total composition. For mousses, the level of propellant is generally from about 3% to about 30% and more preferably from about 5% to about 15% by weight of the total composition.

Alternatively, pressurized aerosol dispensers can be used where the propellant is separated from contact with the hair styling composition such as a two compartment can of the type sold under the tradename SEPRO from American National Can Corp.

Other suitable aerosol dispensers are those characterized by the propellant being compressed air which can be filled into the dispenser by means of a pump or equivalent device prior to use. Such dispensers are described in U.S. Pat. Nos. 4,077,441, Mar. 7, 1978, Olofsson and 4,850,577, Jul. 25, 1989, TerStege, both incorporated by reference herein, and in U.S. Ser. No. 07/839,648, Gosselin et al., filed Feb. 21, 1992, also incorporated by reference herein. Compressed air aerosol containers suitable for use herein include those previously marketed by The Procter & Gamble Company under their tradename VIDAL SASSOON AIRSPRAY® hair sprays.

Furthermore, non-aerosol foams may also be mixed with the present compositions such that the final composition is dispensable as a stable foam. A composition is "dispensable as a stable foam" when it produces a foam when dispensed from a package or container which is either pressurized or equipped with an air or gas mixing device like the F2 non-aerosol foamer described in U.S. Pat. Nos. 5,271,530; 5,337,929; and 5,443,569; all of which are herein incorporated by reference.

g) Silicone Polyether Surfactant

Compositions of the present invention may contain a silicone polyether suitable for stabilizing the organopolysiloxane emulsion. The silicone polyether comprises a polymeric portion comprising repeating organosiloxane units, and a polymeric portion comprising repeating alkylene oxide units (i.e., a silicone-polyoxyalkylene copolymer). Suitable silicone polyethers are those which are surface active in the carrier employed in the compositions of the invention. As will be understood in the art, the surface activity of the silicone polyether will depend on the molecular weight of the polymeric portion comprising repeating organosiloxane units. This portion should be of sufficiently large molecular weight such that it is insoluble in the carrier, yet not so large that it renders the whole molecule insoluble in the carrier. When used, the silicone polyether is preferably used in an amount of from about 0.02% to about 7%, more preferably about 0.05% to about 5%, of the total composition.

The silicone polyether may be a silicone—linear polyoxyalkylene block copolymer (wherein the polymeric backbone comprises silicone blocks and polyoxyalkylene blocks, optionally having grafts), a silicone—graft polyoxyalkylene copolymer (wherein the polymeric backbone comprises silicone blocks and the polyoxyalkylene blocks are present as grafts rather than in the backbone), or a mixture thereof. Linear polyoxyalkylene block copolymers are preferred.

Preferred silicone linear block polyethers suitable for use herein have the formula (I):

$$M'D_bD'_cM'$$

wherein

M' is a monofunctional unit $R_2R'SiO_{1/2}$;

D is a difunctional unit $R_2SiO_{2/2}$;

D' is a difunctional unit $RR'SiO_{2/2}$;

R is independently H, $C_1$–$C_6$ alkyl, or aryl, preferably H or $C_1$–$C_4$ alkyl, more preferably $CH_3$;

R' is independently, an oxyalkylene containing moiety, H, or $CH_3$;

b is an integer of from about 10 to about 1000, preferably about 10 to about 500, more preferably about 20 to about 200; and c is an integer of from 0 to about 100, preferably 0 to about 50, more preferably c is 0, provided that when c is 0, at least one M' contains an oxyalkylene moiety.

Preferred R' in structure (I) are those having the formula:

wherein

R" is a divalent radical for connecting the oxyalkylene portion of moiety R' to the siloxane backbone, preferably —$(C_mH_{2m})$—, wherein m is an integer of from 2 to 8, preferably from 2–6, more preferably from 3–6;

R'" is a terminating radical for the oxyalkylene portion of the moiety R', e.g., H, hydroxyl, $C_1$–$C_6$ alkyl, aryl, alkoxy (e.g., $C_1$–$C_6$) or acyloxy (e.g., $C_1$–$C_6$), preferably hydroxyl;

n is an integer of from 2 to 4, preferably 2 to 3 (i.e., the oxyalkylene group may contain ethylene oxide, propylene oxide and/or butylene oxide units); and y is 1 or greater, wherein the total y from all the oxyalkylene moieties in the copolymer surfactant is 10 or greater.

The oxyalkylene moiety of R' may be a random copolymer, block copolymer or a mixture thereof. Preferred R' groups in structure (I) are those wherein the oxyalkylene units are selected from ethylene oxide units (EO), propylene oxide units (PO), and mixures thereof. More preferred are those wherein the oxyalkylene units have an ethylene oxide unit (EO) to propylene oxide unit (PO) ratio of $EO_{10-100}PO_{0-100}$, more preferably $EO_{20-70}PO_{20-70}$, most preferably $EO_{30-70}PO_{30-70}$, based on the total oxyalkylene in the silicone polyether.

Particularly preferred silicone polyethers are those having the formula:

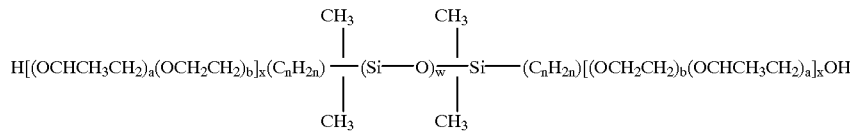

wherein n is an integer of from 2 to 4, x is an integer of 1 or greater; a and b independently are an integer of from about 15 to about 30; and w is an integer of from about 20 to about 200. Such silicone polyethers are commercially available from Goldschmidt Chemical Company under the tradename TEGOPREN 5830.

Preferred silicone graft polyethers for use herein are those having the formula (II):

wherein:

M is a monofunctional unit $R_3SiO_{1/2}$,

D is a difunctional unit $R_2SiO_{2/2}$,

D' is a difunctional unit $RR'SiO_{2/2}$,

R is independently H, $C_1$–$C_6$ alkyl, or aryl, preferably H or $C_1$–$C_4$ alkyl, more preferably $CH_3$, R' is an oxyalkylene containing moiety, b is an integer of from about 10 to about 1000, preferably about 100 to about 500 c is an integer of from 1 to about 100, preferably 1 to about 50.

Preferred R' are those having the formula

wherein

R" is a divalent radical for connecting the oxyalkylene portion of moiety R' to the siloxane backbone, preferably —$(C_mH_{2m})$—, wherein m is an integer of from 2 to 8, preferably 2–6, more preferably 3–6;

R'" is a terminating radical for the oxyalkylene portion of moiety R', e.g., H, hydroxyl, $C_1$–$C_6$ alkyl, aryl, alkoxy (e.g., $C_1$–$C_6$) or acyloxy (e.g., $C_1$–$C_6$), preferably hydroxy or acyloxy, more preferably hydroxyl;

n is an integer of from 2 to 4, preferably 2 to 3 (i.e., the oxyalkylene group may contain ethylene oxide, propylene oxide and/or butylene oxide units); and y is 1 or greater.

The oxyalkylene moiety of R' may be a random copolymer, block copolymer, or a mixture thereof. Preferred R' groups are those wherein the oxyalkylene units are selected from ethylene oxide units (EO), propylene oxide units (PO), and mixtures thereof. More preferred are those wherein the oxyalkylene units have an ethylene oxide unit (EO) to propylene oxide unit (PO) ratio of $EO_{10-100}PO_{0-100}$, more preferably $EO_{10-30}PO_{1-30}$, based on the total oxyalkylene in the silicone polyether.

In this regard, Table 1 shows some representative silicone graft polyethers:

TABLE 1

| Silicone Polyether* | Structure | Weight % EO | Weight % PO | HLB** |
|---|---|---|---|---|
| A | EO | 19 | 0 | 6.8 |
| B | EO | 40 | 0 | 8.0 |
| C | EO/PO | 34 | 0.4 | 6.8 |
| D | EO/PO | 41 | 12 | 8.2 |
| E | EO/PO | 34 | 39 | 5.0 |
| F | EO/PO | 32 | 42 | 6.4 |
| G | EO/PO | 30 | 40 | 5.7 |

*Silicone Polyethers A and B contain less than 20 D units and less than 5 D' units. Silicone Polyethers C-G contain from 100–200 D units and 10–30 D' units.
**Hydrophilic lipophilic balance (HLB) is determined by calculating the weight percent of EO and dividing this value by five.

Silicone polyethers of this type are further described in the above referenced patent application Ser. No. 08/929,721.

Siloxane-oxyalkylene copolymers, i.e., silicone polyethers, can be prepared according to methods generally described in the standard text on silicone chemistry entitled "Chemistry and Technology of Silicones," by Walter Noll, Academic Press Inc., Orlando, Fla., (1968), on pages 373–376. Silicone polyethers are also available from a number of commercial sources such as:

| Trade Name | Supplier | Silicone Content % | EO and/or PO | Molecular Weight |
|---|---|---|---|---|
| D.C.Q2-5220 | Dow Corning[1] | 14 | EO & PO | 3102 |
| D.C.193 | Dow Corning[1] | 33 | EO | — |
| D.C.190 | Dow Corning[1] | 24 | EO & PO | 2570 |
| D.C. Q4-3667 | Dow Corning[1] | 37 | EO | 2400 |
| Silwet L-7200 | OSI[2] | 31 | EO & PO | 19,000 |
| Tegopren 5830/ Abil B8830 | Goldschmidt A.G.[3] | 55 | 40% EO/60% PO | 7800 |
| Tego 5830 - A | Goldschmidt A.G.[3] | 50 | 30% EO/70% PO | 9000 |
| Tego 5830 - B | Goldschmidt A.G.[3] | 50 | 60% EO/40% PO | 9000 |
| Abil B8851 | Goldschmidt A.G.[3] | — | EO & PO | >1400 |
| Abil B8863 | Goldschmidt A.G.[3] | — | EO & PO | >3000 |
| Abil EM 97 neat | Goldschmidt A.G.[3] | 75 | 60% EO/40% PO | 14,000–15,000 |

[1] Dow Corning of Midland, Michigan
[2] OSI Specialties of Lisle, Il.,
[3] Hopewell, VA From the above table, Tegopren 5830-B is preferred in compositions containing relatively high alcohol levels (e.g., >≈40%).

Other silicone polyethers are available as SF-1188 offered by General Electric of Waterford, N.Y., and KF353A offered by Shin Etsu Silicones of America of Torrance, Calif. Additional silicone polyethers are described in U.S. Pat. No. 4,871,529, incorporated herein by reference.

Method of Making

The compositions of the present invention, including personal care compositions, can be made using conventional formulation and mixing techniques. In a preferred method, the silicone functional polymer and preferably any other polymers (e.g., hair styling polymers or hair conditioning polymers), and the solvent are mixed to provide a homogeneous mixture. Any other ingredients are then added and mixed to yield the final composition. If the polymers are neutralized, the neutralizer is preferably added prior to addition of other ingredients. For hair spray products, the composition is packaged in conventional mechanical pump spray devices, or alternatively, in the case of aerosol sprays products, the composition is packaged in conventional aerosol canisters along with an appropriate propellant system (also applicable for mousses). Other hair styling compositions including tonics, lotions, and gels, are typically packaged in a conventional bottle or tube.

High water products, containing less than about 50% VOC, such as mousse (16% VOC or less) and gel (6% VOC or less), and containing a silicone hair styling copolymer derived from monomers containing acid functional groups are preferably prepared in the following manner. The hair styling polymer is dissolved in a compatible, organic solvent, e.g., ethanol or isopropanol, prior to neutralization of the polymer. The solvent used to dissolve the polymer should not contain significant amounts of water and is preferably essentially free of water. If water is added prematurely, either before neutralization or before less than 10% neutralization of the polymer (e.g., neutralization of less than 50% of the acid groups where acid groups are 20% of the polymer structure), the polymer tends to precipitate as a white insoluble mass. Attempts to complete neutralization after precipitation are generally unsuccessful.

Where water is added after neutralization has occurred, the film quality produced from silicone hair styling polymers modified in this manner tends to have a desirable slick and lubricious surface (without intending to be bound by theory, this is usually indicative of silicone present at the surface). Preferred compositions are substantially clear to translucent in appearance. The composition is also stable, preferably retaining within about 10% of its initial clarity with no noticeable precipitate formation for a period of about 6 months or more.

Completion of the neutralization reaction is important for good product clarity, good shampoo removability, and/or good stability of the composition. However, in compositions having low solvent levels and an effective level of the hair styling polymer (1–5%), e.g., in typical mousse and gel formulas, the viscosity of the system can increase dramatically with neutralization. This viscosity increase can hinder completion of the neutralization reaction. Therefore, steps should be taken to ensure that the neutralization reaction is complete. For example, this can be ensured by one or more of the following techniques:

1. When the viscosity of the system becomes very thick (typically when about 10% of the polymer has been neutralized), a portion of the water (preferably a minimum 27% of the batch in 6% VOC systems and minimum 10% of the batch in 16% VOC systems) can be added to the system. The water is used in an amount sufficient to lower the viscosity enough in order to achieve good mixing.

It is preferred from the standpoint of manufacturing efficiency to add the water portion in one step. However, the water may be added in small increments (e.g., 5% of the batch water), between incremental additions of neutralizer. For example, after the first neutralizer addition (sufficient to neutralize up to about 10% of the hair styling polymer) is added with vigorous agitation, then 5% of the batch water can be added, then enough neutralizer to neutralize another 2–4% of the hair styling polymer can be added, then another 5% of the batch water addition can be made. This process continues until all the neutralizer is added to the batch. Application of high shear rates to the system, such as can be generated by a Teckmar type milling device, may also be utilized to increase the mass transfer rate, thereby resulting in faster reaction completeness.

2. When a high viscosity has been reached a specially designed high viscosity mixing device, e.g., a dough mixer, may be used. The system is mixed for many hours until reaction completeness can verified analytically (titration, FTIR, or pH), typically up to about 12 hours. A nitrogen blanketed, enclosed system or the like is preferably used to minimize solvent loss during the mix time.

3. Use specialized pressure vessel equipment, heat and agitation. Heat is to be applied while avoiding evaporation of the solvent. Therefore, a nitrogen blanketed pressure vessel should be employed.

The first and third methods above are preferred as being the most efficient. In the absence of the availability of heated pressure vessels (i.e. ambient conditions), the first method is preferred.

In addition, where the composition contains hydrophobic, oily components such as perfume or isoparaffins, steps must be taken to ensure good emulsification of the hydrophobic component in the composition. However, emulsion compositions containing alcohols can be difficult to formulate. Some hydrophobic components such as those mentioned above are relatively difficult to emulsify, typically requiring very high levels of surfactants in order to create reasonably clear systems (which are typically microemulsions). These high levels of surfactants can over plasticize the hair styling polymer, making it unacceptably sticky.

It has been found in the present invention that the hydrophobic components can be readily emulsified by the use of a combination of organic and inorganic neutralizers. Without intending to be limited by theory, it is believed that this combination of neutralizers help the polymer itself to function as an emulsifier by imparting surfactant-like qualities to the polymer (i.e., a portion of the polymer is relatively hydrophobic and a portion of the polymer is relatively hydrophilic).

The neutralization system comprises a fatty amine neutralizer (preferably selected from dimethyl lauryl amine, dimethyl myristyl amine, amine methyl propanol, dimethylstearyl amine, TEA, and mixtures thereof, more preferably dimethyl lauryl amine, dimethyl myristyl amine and mixtures thereof), in combination with an inorganic neutralizer (preferably metal hydroxides, more preferably NaOH and/or KOH, most preferably NaOH). The amine neutralized acid groups tend to be more hydrophobic than the inorganic neutralized acid groups. Without intending to be bound by theory, it is believed that the amine groups emulsify the hydrophobic components and the inorganic groups provide water solubility/compatibility and shampoo removability.

When such dual neutralizers are employed, the order of component addition and other process variables become important for preparing the clearest, most stable product. The preferred order of addition and process is as follows: With vigorous agitation:

1. Completely dissolve the hair styling polymer in a compatible solvent system containing the water soluble, organic solvent (e.g., ethanol or isopropanol).

2. Add the fatty amine neutralizer in a weight ratio of from 1–6 amine to hydrophobic components to 1–2 amine to hydrophobic components.

3. Add the hydrophobic components.

4. Add any plasticizers.

5. Add the inorganic neutralizer at a level that represents 10%–20% of the hair styling polymer (or 50–100% of the available acid groups in a polymer with 20% acrylic acid).

6. When the system becomes very thick (similar to peanut butter), mix the system for at least 10 minutes. Then add water to the mixture in the manner described above, preferably as described for the preferred embodiment of the first method.

7. Mill the system with a high shear mixer such as made by Teckmar for at least 10 minutes.

8. Add the balance of the water and other ingredients required to make the final composition. Gels are preferably dearated, more preferably before the addition of any thickeners.

It is important to add the silicone emulsions to the system when some water (or other polar material) is present. The water helps to maintain the stability of the silicone emulsions in the composition.

It is preferred to premix the silicone functional polymer with the silicone emulsion prior to making the final compositions hereof. Where the silicone functional polymer is not dispersible in the emulsion, it is preferably mixed in about an equal portion of water containing from 10–50% $C_1$–$C_3$ monohydric alcohol, preferably ethanol, prior to combination with the silicone emulsion. This pre-mix is then added to the other ingredients of the composition which have preferably been pre-mixed. For high monohydric alcohol systems (> about 80%), it is also desirable to premix the silicone emulsion with the silicone finctional polymer prior to combination with the alcohol.

Additionally, it is desirable to not impart high shear rates to the composition once the silicone emulsion has been added, since shear might break the emulsion. Also, the silicone emulsion is typically added after any thickeners or surfactants emulsion.

Method of Use

The compositions of the present invention are used in conventional ways in the intended applications, including personal care products (including hair care, skin care and nail care products), household care products, automotive care products and coating products.

The compositions hereof are useful, for example, in hair styling applications. Such applications generally involve application of an effective amount of the product to dry, slightly damp, or wet hair before and/or after the hair is dried and arranged to a desired style. Application of the product is normally effected by spraying or atomizing the product using an appropriate device, e.g. a mechanical pump spray, a pressurized aerosol container, or other appropriate means. Other hair styling compositions including tonics, lotions, and gels, are typically dispensed from a conventional bottle or tube, and applied directly to the hair or first dispensed to the hand and then to the hair. The composition is then dried or allowed to dry. By "effective amount" is meant an amount sufficient to provide the hair hold and style benefits desired. In general, from about 0.5 g to about 30 g of product is applied to the hair, depending upon the particular product formulation, dispenser type, length of hair, and type of hair style.

Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name.

I. An insect repellent is prepared.

| Component | Weight % |
|---|---|
| Dimethyl phthalate | 20 |
| n-butyl mesityl oxide oxalate | 4 |
| Diethylene glycol monobutyl ether | 5 |
| Polysorbate 20 | 10 |
| Distilled water | 8.7 |
| SDA40 ethanol | 40 |
| Premix | |
| Silicone Functional Polymer - acrylic acid/n-butylmethacrylate/(polydimethylsiloxane (PDMS) macromer-3,000 molecular weight) (50/10/40 w/w/w), M.W. = 20,000 | .90 |
| 30% NaOH in water | .40 |
| Distilled water | 8.00 |
| D.C.2-1845* | 3.00 |
| | 100.00 |

*Silicone microemulsion (25% silicone) from Dow Corning

The batch is prepared by preparing a premix where the water and NaOH are first blended. The silicone functional polymer is then added and stirred for 1 hour. The silicone emulsion is then added and well mixed. The remaining ingredients are put in a separate vessel and well mixed. The premix is then added to the main mix and stirred until homogeneous.

II. An aftershave stick lotion is prepared.

| Component | Weight % |
|---|---|
| SDA40, ethanol | 75.0 |
| Sodium stearate | 6.0 |
| Glycerol | 4.0 |
| Propylene glycol | 3.0 |
| Perfume | 0.3 |
| Menthol | 0.10 |
| Distilled water | 6.10 |
| Premix | |
| Abil Si-6431* | 1.00 |
| SDA 40 ethanol | 1.00 |
| Distilled water | 1.00 |
| DC 2-1550** | 2.5 |
| | 100.00 |

*Available from Goldschmidt
**Silicone microemulsion (25% silicone) from Dow Corning The Abil, water and ethanol are blended and stirred until well mixed. The microemusion is added and stirring continues until it is well mixed. The premix is then added to the main mix after all the others have been added and well mixed. The batch is then heated until the sodium stearate has dissolved and then cooled down to form a stick.

III. An afterbath splash is made.

| Component | Weight % |
|---|---|
| Distilled water | 25.9 |
| Perfume oil | 2.50 |
| Silicone Functional Polymer - N,N-dimethylacrylamide/isobutyl methacrylate/(PDMS macromer - 2,000 molecular weight) (35/5/60 w/w/w), M.W. = 10,000 | 0.50 |
| D.C.2-1716* | 1.00 |
| Laureth-23 | 0.30 |
| SDA 40 ethanol | 69.80 |

*Silicone microemulsion from Dow Corning

The silicone functional polymer and DC2-1716 are premixed until well blended and added to the main mix after all the other ingredients have been added and mixed.

IV. A nail enamel remover is made.

| Component | Weight % |
|---|---|
| Ethyl acetate | 27.00 |
| Propylene glycol | 10.00 |
| Isopropyl alcohol | 25.00 |
| Acetone | 27.00 |
| Distilled water | 8.00 |
| Premix | |
| Silicone Functional Polymer - t-butylacrylate/acrylic acid/ DMS macromer - 3,000 molecular wt) (40/40/20 w/w/w), M.W.= 12,000 | 0.50 |
| Aminomethylpropanol | 0.15 |
| Distilled water | 2.00 |
| D.C.2-8676* | 0.50 |

*Silicone microemulsion from Dow Corning

The silicone functional polymer is blended with the water and aminomethylpropanol until well mixed. The microemulsion is then added and stirred well. The premix is then added to the main mix after all the other ingredients have been well mixed.

V. A hair spray composition is made.

| Component | Example V % |
|---|---|
| SDA 40 Alcohol | 80.00 |
| Amphomer 28-4910(1) | 4.00 |
| Aminomethylpropanol(2) | 0.72 |
| Silicone emulsion/ Surfactant Premix 1A | 2.20 |
| Distilled Water | 13.08 |
| Total | 100.00 |
| Silicone emulsion/ Surfactant Premix | 2A |
| DC-2-1550(3) | 50.00 |
| Abil Si-6431(4) | 8.00 |
| SDA 40 Ethanol | 21.00 |
| Distilled Water | 21.00 |
| Total | 100.00 |

(1)Commercially available from National Starch
(2)Commercially available from Angus
(3)Silicone microemulsion available from Dow Corning
(4)Available from Goldschmidt(a triblock copolymer, 3000 M.W. poly (ethyl oxazoline)-3000 M.W. poly(dimethyl siloxane)- 3000 M.W. poly (ethyl oxazoline)

Silicone Microemulsion Premix: Mix the Abil into ethanol/water until thoroughly mixed. Add the microemulsion and stir until well blended.

Main Mixing: Add Amphomer to alcohol with vigorous agitation to aid in dispersing. Once dissolved, add aminomethylpropanol followed by DRO water (if used) with moderate agitation. Add the silicone microemulsion premix with moderate agitation and stir for additional ½ hour to allow thorough mixing.

VI.–VIII. A fabric softening pump spray composition (VI), a leather conditioner composition (VII), and a pump spray lubricant for machinery (VIII) are made:

| Component | Example V % | Example VII % | Example VII % |
|---|---|---|---|
| SDA Ethanol | 65.00 | 60.00 | 79.00 |
| Perfume | 1.25 | 0.10 | — |
| Distilled Water | Q.S. | Q.S. | — |
| Glycerine | — | 10.00 | — |
| Premix | | | |
| N,N-dimethylacrylamide/isobutyl methacrylate/(PDMS macromer - 2,000 molecular weight) (35/5/60 w/w/w), M.W. = 10,000 | 0.90 | — | — |
| DC-2-1845-HIPV(1) | — | — | 12.00 |
| DC-2-1550(2) | 3.00 | 2.00 | — |
| Abil Si-6431(3) | — | 0.40 | 3.00 |
| SDA Ethanol | — | 0.40 | 3.00 |
| Distilled Water | — | 0.40 | 3.00 |

(1)Silicone microemulsion from Dow Corning with a high internal phase viscosity of 250,000 cps
(2)Silicone microemulsion from Dow Corning
(3)A triblock copolymer from Goldschmidt of 3000 M.W. (polyethyl oxazoline)- 3000 M.W. (polydimethyl siloxane)- 3000 M.W. (polyethyl oxazoline)

Method of Making

Example VI—The silicone functional polymer and microemulsion are premixed for one hour. The remaining ingredients are added and stirred until well blended, after which the premix is added with continued stirring until well mixed.

Examples VII and VIII—The Abil is added to the water and ethanol and stirred until blended at which time the microemulsion is added with continued stirring. This premix is then added to the main mix, which has the remaining ingredients already well mixed. Stirring continues for one-half hour.

IX. Synthesis of Surface Active (Meth)Acrylate-Silicone-(Meth)Acrylate Triblock copolymers A (meth)acrylate-silcone-(meth)acrylate triblock copolymer is prepared according to the method described in "Development of Novel Attachable Initiator for Living Radical Polymerization and Synthesis of Polysiloxane Block Copolymer;" Yoshiki Nakagawa and Krzysztof Matyjaszewski; pages 270–271; Polymer Preprints, August 1996. Some modifications to the method are made and are described in detail below.

Vinyldimethylsilyl terminated polydimethylsiloxane is prepared according to the method described in the above noted reference. The vinyl terminated polydimethylsiloxanes of various molecular weights are obtained from Gelest, Inc., 612 William Leigh Drive, Tullytown, Pa. 19007-6308. Two different vinyldimethylsilyl terminated polydimethylsiloxanes are prepared using vinyl terminated polydimethylsiloxanes of molecular weights 9,400 and 6,000 with percent vinyl substitution of 0.8–1.2 and 0.4–0.6, respectively.

a) Block Copolymer Synthesis: Poly(n-butyl acrylate-co-methacrylic acid)-block-Polydimethylsiloxane-Poly(n-butyl acrylate-co-methacrylic acid)

Into an argon purged round-bottomed flask equiped with a magnetic strrer and reflux condenser, is added butyl acetate (500 ml), vinyldimethylsilyl terminated polydimethylsiloxane (18 g), CuCl (0.66 g), 4,4'-dinonylbipyridyl (5.4 g), butyl acrylate (9 g), and trimrthylsilylmethacrylate (9 g). The solution is then heated to 120° C. with stirring for 6 hours. The solution is then cooled to ambient temperature and catalyst is removed via vacuum filtration. The filtrate is diluted with acetone (100 ml). The resulting solution is precipitated into water and the block copolymer is collected and dried.

Similar polymers are prepared in the same manner using polydimethylsiloxane of different molecular weights and acrylate outer blocks with various monomer combinations, e.g. variety of esters derived from acrylic and methacrylic acids such as described herein. The monomers of the acrylate outer blocks may be selected such that the outer blocks have a Tg above or below ambient temperature (about 23° C.).

What is claimed is:

1. A personal care composition suitable for application to the hair, skin or nails comprising:

a) a silicone functional polymer having the formula selected from the group consisting of:

$(AB)_n$; ABA; BAB;

and mixtures thereof;

wherein B is a silicone moiety comprising repeating units of:

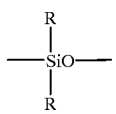

R is independently, C1–C30 alkyl, aryl, alkylaryl, haloalkyl, H, or C1–C6 alkoxy, wherein the weight average molecular weight of each silicone moiety B is independently from about 1500 to about 50,000;

A is a polar polymeric moiety which is soluble or dispersible in mixtures of ethanol and water containing less than 60% ethanol by weight;

n is an integer of 1 or greater;

wherein the molecular weight of the silicone functional polymer is at least about 2,000;

b) an organopolysiloxane emulsion comprising:

(i) a polyorganosiloxane dispersed as particles in the emulsion, the polyorganosiloxane having an average particle size of less than about 150 nanometers, wherein the polyorganosiloxane contains the difunctional repeating unit which corresponds to the general formula:

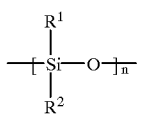

wherein n is greater than 1 and $R^1$ and $R^2$ are each independently $C_1$–$C_7$ alkyl or phenyl, and wherein the degree of polymerization of the polysiloxane is in the range of from 10 to 3,000; and (ii) a surfactant system for dispersing the organopolysiloxane in the emulsion;

c) a carrier comprising (i) at least about 0.5%, by weight of the composition, of a first solvent selected from the group consisting of: water; water soluble organic solvents; organic solvents which are strongly to moderately strong in hydrogen-bonding parameter; and mixtures thereof; wherein the first solvent is other than $C_1$–$C_3$ monohydric alcohol, $C_1$–$C_3$ ketone and $C_1$–$C_3$ ether, and (ii) at least about 40%, by weight of the composition, of a second solvent selected from the group consisting of $C_1$–$C_3$ monohydric alcohols, $C_1$–$C_3$ ketones, $C_1$–$C_3$ ethers, and mixtures thereof;

wherein the silicone functional polymer is present in an amount effective to stabilize the emulsion in the personal care composition.

2. The composition of claim 1 wherein the weight average molecular weight of each silicone moiety B is independently from about 2,000 to about 40,000.

3. The composition of claim 2 wherein the weight average molecular weight of each silicone moiety B is independently from about 2,000 to about 30,000.

4. The composition of claim 1 wherein A is selected from the group consisting of acrylic polymers, vinyl polymers, polyalkyloxazolines, proteins, sugars, polysaccharides and mixtures thereof.

5. The composition of claim 4 wherein A is selected from the group consisting of acrylic polymers, vinyl polymers, polyalkyloxazolines, and mixtures thereof.

6. The composition of claim 1 wherein the molecular weight of the silicone functional polymer is from about 2,000 to about 150,000.

7. The composition of claim 6 wherein the molecular weight of the silicone functional polymer is from about 3,000 to about 50,000.

8. The composition of claim 7 wherein the molecular weight of the silicone functional polymer is from about 3,000 to about 20,000.

9. The composition of claim 1 wherein the silicone functional polymer is a silicone graft copolymer having a vinyl polymeric backbone comprising acrylate groups having grafted to it monovalent siloxane polymeric moieties, the copolymer comprising C monomers and components selected from the group consisting of A monomers, B monomers, and mixtures thereof, wherein:

A is at least one free radically polymerizable vinyl monomer, the amount by weight of A monomer, when used, being up to about 90% by weight of the total weight of all monomers in said copolymer;

B is at least one reinforcing monomer copolymerizable with A, the amount by weight of B monomer, when used, being up to about 98% of the total weight of all monomers in said copolymer, said B monomer being selected from the group consisting of polar monomers and macromers;

at least one of said A or B monomers comprising acrylate groups; and

C is a polymeric monomer having a weight average molecular weight of from about 1,500 to about 50,000 and the general formula

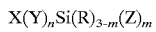

$$X(Y)_n Si(R)_{3-m}(Z)_m$$

wherein

X is a vinyl group copolymerizable with the A and B monomers,

Y is a divalent lining group,

R is a hydrogen, lower alkyl, aryl or alkoxy,

Z is a monovalent siloxane polymeric moiety having a number average molecular weight of at least about 500, is essentially unreactive under copolymerization conditions, and is pendant from said vinyl polymeric backbone after polymerization, n is 0 or 1, m is an integer from 1 to 3, wherein C comprises from about 0.01% to about 50% by weight of the copolymer.

10. The composition of claim 9 wherein the silicone functional polymer is selected from the group consisting of:

(A) acrylic acid/n-butylmethacrylate/(polydimethylsiloxane (PDMS) macromer-3,000 molecular weight) (50/10/40 w/w/w), M.W.=20,000;

(B) N,N-dimethylacrylamide/isobutyl methacrylate/(PDMS macromer-2,000 molecular weight) (35/5/60 w/w/w), M.W.=10,000;

(C) N,N-dimethylacrylamide/(PDMS macromer-4,000 molecular weight) (80/20 w/w), M.W.=20,000;

(D) t-butylacrylate/acrylic acid/(PDMS macromer-3,000 molecular weight) (40/40/20 w/w/w), M.W.=12,000;

(E) t-butylacrylate/acrylic acid/(PDMS macromer-12,000–14,000 molecular weight) (65/25/10 w/w/w), M.W.=80,000; and (F) mixtures thereof.

11. The composition of claim 1 wherein A is a polyalkyloxazoline.

12. The composition of claim 11 wherein the silicone functional polymer is a triblock copolymer of 3000 M.W. (polyethyl oxazoline)-3000 M.W. (polydimethyl siloxane)-3000 M.W. (polyethyl oxazoline).

13. The composition of claim 1 wherein the average particle size of the dispersed polyorganosiloxane is about 60 nanometers or less.

14. The composition of claim 13 wherein the average particle size of the dispersed polyorganosiloxane is about 40 nanometers or less.

15. The composition of claim 1 wherein the first solvent is water.

16. The composition of claim 1 wherein the second solvent is a $C_1$–$C_3$ monohydric alcohol.

17. The composition of claim 16 wherein the monohydric alcohol is selected from the group consisting of ethanol, n-propanol, isopropanol and mixtures thereof.

18. The composition of claim 17 wherein the first solvent is water.

19. The composition of claim 1 wherein the composition comprises from about 0.01% to about 20% of the silicone functional polymer.

20. The composition of claim 19 wherein the amount of emulsion is such that the personal care composition comprises from about 0.01% to about 10% of the dispersed polyorganosiloxane.

21. An emulsion composition comprising:

a) a silicone functional polymer having the formula selected from the group consisting of:

$(AB)_n$; ABA; BAB;

and mixtures thereof;

wherein B is a silicone moiety comprising repeating units of:

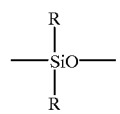

R is independently, C1–C30 alkyl, aryl, alkylaryl, haloalkyl, H, or C1–C6 alkoxy, wherein the weight average molecular weight of each silicone moiety B is independently from about 1500 to about 50,000;

A is a polar polymeric moiety which is soluble or dispersible in mixtures of ethanol and water containing less than 60% ethanol by weight;

n is an integer of 1 or greater;

wherein the molecular weight of the silicone functional polymer is at least about 2,000;

b) an organopolysiloxane emulsion comprising:

(i) a polyorganosiloxane dispersed as particles in the emulsion, the polyorganosiloxane having an average particle size of less than about 150 nanometers, wherein the polyorganosiloxane contains the difunctional repeating unit which corresponds to the general formula:

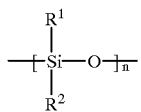

wherein n is greater than 1 and $R^1$ and $R^2$ are each independently $C_1$–$C_7$ alkyl or phenyl, and wherein the degree of polymerization of the polysiloxane is in the range of from 10 to 3,000; and (ii) a surfactant system for dispersing the organopolysiloxane in the emulsion;

c) a carrier comprising (i) at least about 0.5%, by weight of the composition, of a first solvent selected from the group consisting of water; water soluble organic solvents; organic solvents which are strongly to moderately strong in hydrogen-bonding parameter; and mixtures thereof; wherein the first solvent is other than $C_1$–$C_3$ monohydric alcohol, $C_1$–$C_3$ ketone and $C_1$–$C_3$ ether, and (ii) at least about 40%, by weight of the composition, of a second solvent selected from the group consisting of $C_1$–$C_3$ monohydric alcohols, $C_1$–$C_3$ ketones, $C_1$–$C_3$ ethers, and mixtures thereof;

wherein the silicone functional polymer is present in an amount effective to stabilize the emulsion in the composition.

22. A personal care product containing the emulsion of claim 21.

23. A household care product containing the emulsion of claim 21.

24. An automotive care product containing the emulsion of claim 21.

25. A coating product containing the emulsion of claim 21.

* * * * *